(12) United States Patent
Bietz et al.

(10) Patent No.: US 10,149,634 B2
(45) Date of Patent: Dec. 11, 2018

(54) MOBILE DEVICE AND CASE FUNCTIONALLY AND PHYSICALLY COUPLED TO THE MOBILE DEVICE

(71) Applicants: Steven Lee Bietz, Cypress, TX (US); Jesus Acosta-Cazaubon, Rochester, NY (US)

(72) Inventors: Steven Lee Bietz, Cypress, TX (US); Jesus Acosta-Cazaubon, Rochester, NY (US)

(73) Assignee: Voll, Inc., Cypress, TX (US)

( * ) Notice: Subject to any disclaimer, the term of this patent is extended or adjusted under 35 U.S.C. 154(b) by 436 days.

(21) Appl. No.: 15/086,204

(22) Filed: Mar. 31, 2016

(65) Prior Publication Data

US 2017/0202481 A1 Jul. 20, 2017

Related U.S. Application Data

(63) Continuation-in-part of application No. 14/997,559, filed on Jan. 17, 2016, now Pat. No. 9,332,390.

(51) Int. Cl.
*A61B 5/07* (2006.01)
*H04B 1/3888* (2015.01)
(Continued)

(52) U.S. Cl.
CPC ........... *A61B 5/073* (2013.01); *A61B 8/08* (2013.01); *H04B 1/385* (2013.01); *H04B 1/3877* (2013.01);
(Continued)

(58) Field of Classification Search
CPC ....... H04W 4/008; H04W 64/00; H04W 4/02; H04W 29/08657; H04W 4/023; H04W 56/0025; H04W 4/80; H04B 1/3888; H04B 1/3877; H04B 1/385; G01S 5/0252; G01S 5/02; A61B 5/073; A61B 8/08

See application file for complete search history.

(56) References Cited

U.S. PATENT DOCUMENTS

| 8,690,600 | B1 * | 4/2014 | Zeolla | G06F 1/1628 |
| | | | | 439/131 |
| 2005/0093709 | A1 * | 5/2005 | Franco, Jr. | A61B 5/1112 |
| | | | | 340/686.1 |

(Continued)

OTHER PUBLICATIONS

Vincent Chan and Anahi Perlas, Basics of Ultrasound Imaging, S.N. Narouze (ed.), Atlas of Ultrasound-Guided Procedures in Interventional Pain Management, DOI 10.1007/978-1-4419-1681-5_2, © Springer Science+Business Media, LLC 2011, 2011, XXVIII, 372 p. 465 illus., 350 illus. in color., Hardcover, ISBN: 978-1-4419-1679-2.

*Primary Examiner* — Ted M Wang
(74) *Attorney, Agent, or Firm* — Tracy Jong Law Firm; Tracy P. Jong; Cheng Ning Jong

(57) ABSTRACT

A mobile device case for functional connection and physical attachment to a mobile device, the mobile device case comprises an application adapted to run in the mobile device and a cradle configured for removable attachment with the mobile device, the cradle comprising a controller capable of functional connection with the application, where the cradle is adapted to protect the mobile device while attached to the mobile device and the cradle is adapted to functionally pair with the application to create at least a portion of a mesh network.

32 Claims, 22 Drawing Sheets

(51) Int. Cl.
    *A61B 8/08*       (2006.01)
    *H04B 1/3877*    (2015.01)
    *H04W 4/02*      (2018.01)
    *H04B 1/3827*    (2015.01)
    *H04W 4/80*      (2018.01)
    *H04W 84/18*     (2009.01)
    *H04W 56/00*     (2009.01)

(52) U.S. Cl.
    CPC .......... *H04B 1/3888* (2013.01); *H04W 4/023* (2013.01); *H04W 4/80* (2018.02); *H04W 56/0025* (2013.01); *H04W 84/18* (2013.01)

(56) References Cited

U.S. PATENT DOCUMENTS

| | | | |
|---|---|---|---|
| 2005/0201340 A1* | 9/2005 | Wang | H04L 41/046 370/337 |
| 2011/0195753 A1 | 8/2011 | Mock et al. | |
| 2011/0312270 A1* | 12/2011 | White | H04M 1/0274 455/41.1 |
| 2013/0033358 A1 | 2/2013 | Yamazaki et al. | |
| 2013/0146661 A1 | 6/2013 | Melbrod et al. | |

* cited by examiner

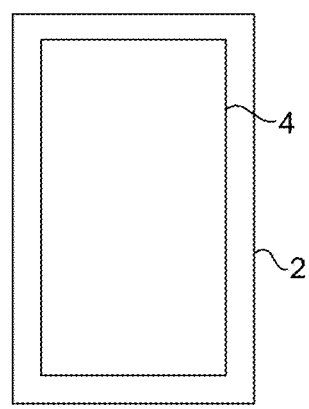
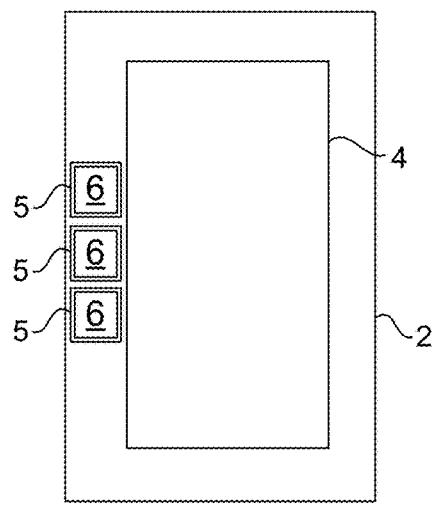
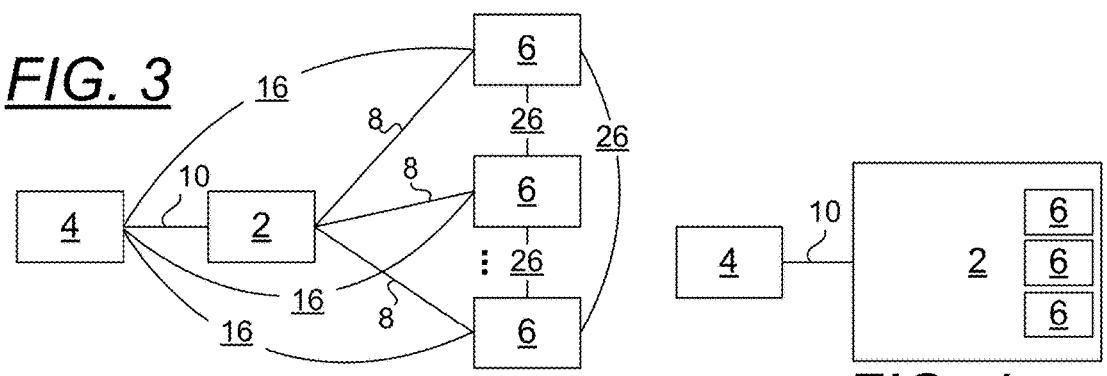
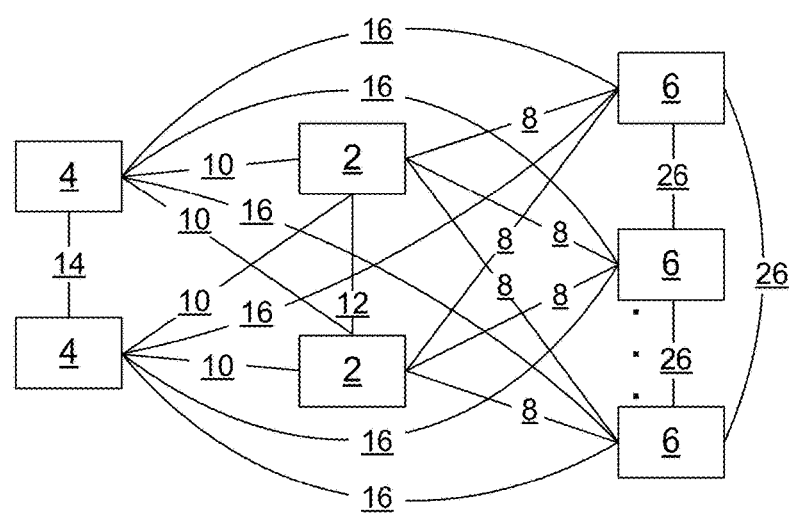

MOBILE DEVICE AND CASE FUNCTIONALLY AND PHYSICALLY COUPLED TO THE MOBILE DEVICE

PRIORITY CLAIM AND RELATED APPLICATIONS

This continuation-in-part application claims the benefit of priority from application U.S. Ser. No. 14/997,559 filed on Jan. 17, 2016. Said application is incorporated by reference in its entirety.

BACKGROUND OF THE INVENTION

1. The Field of the Invention

The present invention is directed generally to a system for enabling personal security, localization and health monitoring. More specifically, the present invention is directed to a system for enabling personal security and health monitoring that is coupled to a ubiquitous mobile device and a localization system not dependent on a Global Positioning System (GPS) network.

2. Background Art

Modern day localization methods typically involve the use of Global Positioning System (GPS) which require hardware, e.g., GPS receiver, cell towers, relay towers and other infrastructure to locate immobile or mobile devices. Such methods are not available to underwater applications and can be non-operational on severely overcast days. Low cost mobile personal security monitoring devices have been typically limited to discrete devices that require additional package space for travel. These devices are often limited to simply performing the action of an audio or visual alarm if an event such as the opening of a hotel room door is detected. These monitoring devices also have typically required that human action be taken to call for help. These low cost devices have typically not made use of automated communication through network means to notify various parties for help based on preprogrammed parameters and Global Positioning System (GPS) coordinates. Such low cost personal security devices have not integrated multiple detection methods and aggregated monitoring sensors and devices, located both local and distant, into a convenient and small travel package. Further, they have not included the ability to aggregate additional monitoring devices and to form mesh networks of multiple personal security devices and peripherals through communication means, such as Near Field Communication (NFC), Bluetooth, Wi-Fi and other wireless communication means. They also were not able to aggregate distant monitoring devices through wireless communication to the internet and wireless communication to other devices from the internet to remote aggregated devices. Further, conventional sonograms or tomographs are obtained using a single probe or probes that are grouped in close proximity offering views from similar perspectives. No confirmation of imaged features are available due to the single dimensionality of scanning perspectives. Disclosed below are references in which one or more elements of the present invention may be disclosed but none of which disclose devices used for performing the functions of the present invention.

U.S. Pat. Pub. No. 20130033358 of Yamazaki et al. (hereinafter Yamazaki) discloses a system including at least one sender, and a beacon signal sent from the sender that is received by a portable terminal. In accordance with a sender ID included in the beacon signal, the portable terminal displays on an Liquid Crystal Display (LCD) a map image and a current position of the portable terminal or a user having the portable terminal, and displays on the LCD a guide image as for events or exhibition items in a predetermined place. The portable terminal stores state information included in the beacon signal for each sender (sender ID), and transmits or moves the state information to a central terminal at a predetermined timing. Yamazaki fails to disclose a case capable of physical coupling to a mobile device. Yamazaki further fails to disclose a means by which to detect a large motion or movement and guard against detecting vibrations which are to be ignored. This publication fails to include a mesh network in that senders/nodes do not relay information between each other but only to a portable terminal. Further, the portable terminals do not relay information between each other and are not able to relay information from one terminal to another and back to the central terminal. A mobile terminal is unable to communicate directly to the central terminal. Thus, if a portable terminal loses communication, it cannot relay through another portable terminal. Note also in this disclosure that vibration is used to detect that a sender or node has been moved from a stationary position. A notice of vibration or movement indicates that repositioning and recalibration of Yamazaki's portable terminal is required while the present invention includes senders or nodes that can be continuously moving (as not required to be stationary). Yamazaki fails to disclose localization methods.

U.S. Pat. Pub. No. 20130146661 of Melbrod et al. (hereinafter Melbrod) discloses embodiments of a smart phone casing and information exchange system which enables a user to carry a single system that merges the digital and telecommunications necessities of the individual with the personalized cards, membership accounts, consumer credit and/or medical insurance or health information in a single source protected both physically with a hardened case, and digitally with appropriate safeguards for electronic protection. Melbrod demonstrates the use of a smart phone case capable of storing information and safeguards for allowing certain information exchanges only. It does not however disclose a smart phone case having the tools and means for detecting large motions and movements, etc. Melbrod also fails to disclose localization methods.

U.S. Pat. Pub. No. 20110195753 of Mock et al. (hereinafter Mock) discloses a smart phone case with Light Emitting Diodes (LEDS). In a particular embodiment, the case includes a front portion adapted to cradle a lower portion of a smart phone, a rear portion adapted to engagingly mate with the front portion to secure the smart phone within the case, a first strip of LEDS and a second strip of LEDS that are mounted on opposing sides of the front portion, a vibrating sensor that is adapted to activate the LEDS of the case when a vibrator of the smart phone is vibrating, and circuitry is used to control the vibrating sensor and the LEDS. The vibrating sensor detects vibrations of the vibrator of the smart phone when the smart phone is receiving an incoming call or message. The LEDS are programmed to display in a set sequence when activated, where the set sequence to display the LEDS is selected by a user. Mock demonstrates the use of a case for detecting vibration from a smart phone and taking an action, i.e., activating LEDS based on the detection of the vibration. It does not however disclose a smart phone case having the tools and means for detecting large motion and movements, etc. Mock also fails to disclose localization methods.

Therefore, there arises a need for a mobile system which can be seamlessly coupled with a ubiquitous mobile device for providing personal security and health monitoring and a

SUMMARY OF THE INVENTION

Disclosed herein is a mobile device case for functional connection and physical attachment to a mobile device, the mobile device case includes:
  (a) an application adapted to run in the mobile device; and
  (b) a cradle configured for removable attachment with the mobile device, the cradle including a controller capable of functional connection with the application,
wherein the cradle is adapted to protect the mobile device while attached to the mobile device and the cradle is adapted to functionally pair with the application to create at least a portion of a mesh network.

In one embodiment, the present system further includes at least one sensor functionally connected to the controller.

In one embodiment, the at least one sensor is an accelerometer. In another embodiment, the at least one sensor is a directional antennae. In another embodiment, the at least one sensor is an ultrasound transducer. In yet another embodiment, the at least one sensor is an imaging device.

In one embodiment, the present system further includes at least one socket for receiving at least one sensor, wherein the at least one socket is functionally connected to the controller.

In one embodiment, the functional connection is wired. In another embodiment, the functional connection of the controller of the cradle with the application is wired. In another embodiment, the functional connection of the controller of the cradle with the application is wireless.

In one embodiment, the present system further includes a data transmitter and a data receiver, wherein the data transmitter is adapted to initiate a communication with a data receiver of the mobile device and the data receiver is adapted to receive a communication with a data transmitter of the mobile device.

In one embodiment, the functional connection is made according to Bluetooth. In another embodiment, the functional connection is made according to wireless local area network (Wi-Fi).

In one embodiment, the functional connection includes:
  (a) communicating a message from the controller of the cradle of the mobile device case to the application;
  (b) calculating a time of flight of the message; and
  (c) comparing the time of flight to an expected time of flight to yield a discrepancy,
wherein if the discrepancy is greater than a predetermined value, an action is initiated by one of the application and the mobile device case.

In one embodiment, the functional connection includes:
  (a) communicating a message from the application to the cradle of the mobile device case;
  (b) calculating a time of flight of the message; and
  (c) comparing the time of flight to an expected time of flight to yield a discrepancy,
wherein if the discrepancy is greater than a predetermined value, an action is initiated by one of the application and the mobile device case.

In one embodiment, there is provided a mobile device case that itself can serve as a sensor module that can be removed from the phone and placed for security monitoring (e.g., it can be removed from the phone and with an attached lanyard hung from a room door to detect motion with an integrated accelerometer).

One embodiment of the present invention includes a mobile device case or mobile personal security device (MPSD) constructed so as to function as a mobile device case for devices such as mobile phones, tablets, and other mobile communication devices and peripheral devices thereof and the like. An MPSD may include one or more assembly modules and monitoring capabilities for use in conjunction with a mobile device or mobile communication device (MCD) such as a mobile phone, computer tablet and the like. The MPSD is constructed so as to be able to optionally include one or more sensors or Secure Linked Devices (SLD) that can be decoupled from wired and wireless connections to the MPSD and provide monitoring through a plurality of methods for sensor and other data input into the MPSD. This MPSD device may include, but not limited to, an MCD case having one or more integrated sensors such as an accelerometer and an attachment method such as a lanyard for attaching to a door handle or other object for the purpose of security monitoring. A mobile device case that is removable, functions not only as a proxy or data concentrator to external sensors, but also provides an optimized method of carrying or attaching those sensors for ease and simplicity of transport to a new location. In one embodiment, the present sensors can be attached to or detached by sliding into slots in the case or sliding off from the slots.

This system also functions as a mesh network allowing sensors to relay data to the mobile device or to the "smart case" with the smart case functioning as a proxy and data concentrator. Further, more than one mobile device can be securely paired to the system allowing multiple persons to receive and act upon the data (i.e., two parents, each monitoring children with sensor modules). Note that sensors in a mesh network can form subgroups to allow for, but not limited to, (a) data averaging; (b) focused monitoring such as extra listening sensors attached to a baby's crib to listen for breathing/movement from multiple directions (as a baby may be facing different directions). In one embodiment, this mesh network system is fully mobile and easily moved and set-up at a new location (e.g., a hotel room) as all components including MCDs are mobile.

In one embodiment, the present security system makes use of remote sensors to detect motion, relative distance, and direction of motion through the combination of synchronized clocks, an accelerometer, time of flight between devices and a mobile device (or smart case working as a proxy/data concentrator).

The present security system may not provide accurate location information but such information is suitable for a monitoring system that would provide these parameters for use in keeping a group of kids together, e.g., via sensors attached to each kid in a public venue. Often, in such applications, accurate distance measurements are unnecessary. In some embodiments, compass readings may be utilized to assist in making directional references for the system.

Practical application examples include, but not limited to the following:
(a) A sensor with a Radio Frequency (RF) receiver (Wi-Fi for example), an accelerometer, and its clock synchronized to a system (all devices in the system being synchronized when set-up at a new location) is attached to a door. The accelerometer detects motion and sends an initial alarm signal. The MPSD and/or MCD determines if the motion indicates low or high risk and takes actions based on the interpretation of the data (i.e., an extreme event indicating the door has likely been kicked-in or a small vibration likely due to air movement). As the initial motion has been detected, the second part of the security monitoring comes into play; the detection of relative motion, speed, and change in position of the sensor in order to determine if a security risk exists. This detection is made by comparing the time lapsed between sent and received signals between the MPSD and MCD to determine if there is a security risk. In the example above, only one accelerometer is used. This can lead to false interpretation of small vibrations of the door as low risk and likely just air movement. However, the small vibrations can be the result of an actual tampering of the door lock and slow opening of the door so as not to trigger a security risk assessment. In order to know more precisely if the door has been opened, there is a need for detecting a change in position of the sensor. This is accomplished by determining the time of flight of the signals between the MPSD on the door and the MCD. In this way, a door being tampered with (e.g., lock picked) and opened could be accurately identified and an alarm created. In another embodiment, comparisons of time stamps between the senders and receivers are used to indicate situations of concern.

(b) In a second example, a group of persons are monitored and kept together. For instance, a group of preteens on a field trip are monitored and kept together with two or more teachers. Each preteen can be in possession of a sensor module handed to them by a teacher. The teachers, each having a mobile device linked as part of the mesh network could monitor the relative distance (near, moderate, far), relative rate of travel (relative, not needing a unit reference, and low accuracy but as compared to others in the group), and relative direction of travel (again relative to the need with general direction and low level of accuracy needed).

(c) In a third example, the system could be set-up by placing sensors at stationary locations around a given vacant area where changes in the RF signal characteristics are monitored. Such changes could indicate changes in the time of flight of signals between devices and the possible presence of an intruder. The present system may seek new signals from devices that are not part of the security system indicating the presence of a new signal source that could be an intruder (e.g., a burglar with a cell phone or a remote control device and its new signal being identified as new to the monitored area). This is especially useful in that motion detection by tracking a heat source across zones, e.g., in a traditional security motion sensing situation, would not be necessary and temperature variations (e.g., due to forced air heating sources) in the air would not be a significant factor. Further, movement of non living objects would also be detected preventing remote control devices in possession of intruders from not being detected.

In one embodiment, an MPSD is constructed as a discrete device that can be worn on the body in the form of a MCD case that is worn similarly to a watch in that it attaches to a body limb or other body part and may be decoupled from the MCD providing remote monitoring through a plurality of wireless and wired communications. The MPSD can be coupled to a Brain-computer interface (BCI) and/or wired glove/dataglove/cyberglove" (connected or not to exosuit/ Virtual Reality (VR) glasses/perception extension devices) to improve or help human capabilities.

In one embodiment, an MPSD functionality is integrated into a wristband (watch)/multiple body bands type (bodysuit) device/devices having a plurality of purposes such as, but not limited to, time monitoring, Global Positioning System (GPS) location, heart/oxygen/humidity/sugar levels/ allergy monitoring worn through attachment to a body limb or other body part where this body device and body device extensions allow better conditions for human performance. This capability can be extended to use neurological observations to enable MPSD functionality to automatically administer life-saving treatment such as, but not limited to, applying insulin or cortisone injections. Also this can be used by older people to monitor their health and need for help and provide a way to communicate their needs to a central or multiple computers and networks in a home or other places.

Another embodiment of this invention is the integration of an MPSD into an MCD that is worn through attachment to a body limb similarly to a watch. This MPSD can be a device placed internally to a person's body such as a pacemaker. The MPSD/pacemaker can indicate that the person is in need of help and provide necessary assistance in an exosuit capability for elder people.

Another embodiment of this invention is one or more SLDs that may serve as a case for a MCD or MPSD that is worn in a similar fashion to a watch and attached to a body limb or other body part and may be decoupled from the MCD or MPSD.

Another embodiment of this invention is an MPSD or an MPSD integrated into an MCD that is integrated into a strap, rope, or band form that can be attached in a plurality of methods to a person or other objects and locations.

Another embodiment of this invention is an SLD integrated into a strap, rope, or band form that can be attached in a plurality of methods to a person or other objects and locations.

Another embodiment of this invention is an MPSD constructed so as to be a device with the general appearance of eye glasses.

Another embodiment of this invention is the integration of an MPSD into an MCD that is worn in the general fashion of eye glasses or other visual devices such as goggles including electronic and mechanical assemblies for a plurality of purposes.

Another embodiment of this invention is the integration of one or more SLDs that are worn in the general fashion of eye glasses or other visual devices such as goggles including electronic and mechanical assemblies for a plurality of purposes.

Another embodiment of this invention is an MPSD or an SLD constructed so as to be a device that can be easily concealed through appearing as an item of a different use such as, but not limited to, a button, clasp, or article of adornment such as jewelry.

Another embodiment of this invention is an MPSD, an MPSD integrated into an MCD or an SLD worn as a separate dangling device such as a keychain or keychain attachment in general appearing like a car key fob.

Another embodiment of this invention is an MPSD coupled to an article of clothing so as to provide added functionality such as heart monitoring in a shirt, rate of speed and distance in a shoe, camera observation through a hat, and other forms of data that would be useful for monitoring personal security.

Another embodiment of this MPSD includes one or more cameras that may work separately or in unison with the MCD camera to provide three dimensional (3D) video capture or pictures (this 3D combined with GPS (location information) information can be combined with an exosuit to provide help to elderly people for physical mobility and directional assistance. For example, a combination of robotic assistance and an exosuit/MPSD would allow humans to have a richer live during the elderly years. The capability to use sensory integration/MPSD can allow a better integration between humans and monitoring air and weather health conditions. For example, allergens could be monitored (e.g., pollens) as well as air quality hazards (e.g., pollution) to protect persons sensitive or simply wanting to avoid exposure. For personal security, some sensors in the MPSD system could detect dangerous substances (e.g., poisonous gasses) that can be dangerous and alert the individual and in some circumstances also provide a preventive mechanism such as a filter face mask. The user could view in 3D on the screen by each of two camera views being displayed on ½ of the screen and the case providing a visual divider between the screens when held close to the face of the user, much like looking though a stereo photograph viewer. This MPSD captured video or pictures could be activated by a preprogrammed sensor input or other input for a plurality of monitoring methods. In this way, the holder of the MPSD could also capture pertinent evidence when a disturbance has occurred as well as playback or stream the video or pictures in real time to third parties such as the police. The MPSD may optionally be incorporated into the MCD and function through the use of application software.

Another embodiment of an MPSD is a MCD case optionally including one or more cameras that may work separately or in unison with the MCD to utilize night vision techniques such as, but not limited to, night vision light emitted from an LED and made visible on the screen of the MCD. In this way the MPSD coupled with or separately can provide an emergency night vision device giving persons a better chance of escaping a dangerous situation by using the cover of darkness. The MPSD may optionally be incorporated into the MCD and function through the use of application software.

Another embodiment is an MPSD and/or an SLD as location devices that have their location determined through the use of time of flight measurement to one or more transmitter nodes allowing for its approximate location to be provided to third parties for location monitoring. In yet another embodiment, an MPSD is a location device that has its location determined through the use of signal triangulation allowing for its approximate location to be provided to third parties for location monitoring. More than one MPSD or SLD may be employed to receive and transmit a signal so that an averaging might be used when some signals may be very weak and difficult to use well. Transmitter nodes may be inside buildings such as, but not limited to, Wi-Fi transmitters or external to buildings such as, but not limited to, cellular towers. A smoothing algorithm may be employed to provide more stable time of flight reference. The smoothing algorithm yields smoother linear curves with less extreme vacillation which corresponds better with the actual MPSD/SLD motion. The movement of the MPSD/SLD out of a set of parameters such as, but not limited to, distance from one or more transmitter nodes could be used to trigger a plurality of alarms and methods to request help from third parties.

Another embodiment is a mobile system using time of flight location technology. The use of signal transmission between the MCD and one or more MPSD and one or more SDL would be used. All components of this system could travel easily to a new destination and be set-up into a temporary monitoring system as a new location such as a hotel room. The time of flight of signals between all devices would be measured and used to indicate movement and relative position between devices. For example, a change in a position of a SLD on a door relative to the MCD could cause an alarm (e.g., a person is sleeping in a hotel room with his smart phone (MCD) beside him) to sound an alarm in the MCD but also third party devices through preprogrammed responses (e.g., set-off a hotel alarm or call 911). Another example of use would be for a traveling parent holding a MCD to be able to monitor children having their own MCDs, MPSDs and/or SLD in their possession or attached to their persons. Relative position and likely distance could be monitored to keep a group together and if a member gets too far away to move in their direction to find them (e.g., a metal detector uses signal bounce to lead the user to the metal object, but in this case the seeking MCD uses monitoring of the time of flight of signals to get closer to the person or child holding another MCD, MPSD, or SLD). Further, this approach could be used to identify "good devices" that are known and "bad devices" that are unknown and could be intruders entering into a monitored area. In one use, the MCD could be removed and the MPSD and SLDs could continue to monitor and collect data such as within a hotel room. Upon request, or when a device is triggered, the MPSD and or SLD could provide a report of any changes in movement (e.g., a window or door) or the intrusion or an unknown signal into the monitoring area. The collected data could be provided to one or more MCDs and third parties through a plurality of communication links. For example, a smart phone could remotely access one or more MPSDs and or SLDs to get a security data report and use it to determine if the monitored area has had an intruder. Another example would be for a person outside his hotel room with a smart phone to use Bluetooth protocol to access one or more MPSD and or SLDs within the hotel room to determine if an intruder is present. This could be used in the same way with an automobile.

Any of the MCD, MPSD, or SLD may include a "Find Me" button or alarm functionality. That alarm functionality would employ a plurality of methods to call for help by sending automated alarms to third party monitoring to a call for help signal to another MCD or MPSD (or relayed through another SLD). For example, a mother could use the link between her MCD or MPSD to a SLD attached to her child to monitor distance, but the child could also push the "Find Me" button if they became lost or scared. The mother would receive the alarm and use positioning technologies (e.g., time of flight of signals, triangulation, etc.) to locate the lost child. A voice link could also be established between the MCD and the SLD to provide real time communication to facilitate faster location of the lost child.

An MCD, MPSD, and or SLD could be used as a beacon to allow for return to a given location. For example, in a beacon mode, an MPSD could be left in a given location (e.g., locked to a stationary object) and provide a beacon signal for later returning to the same location. The beacon mode would use a plurality of methods to secure against tampering while in beacon mode such as, but not limited to, fingerprint recognition. The beacon mode could allow others holding an MCD, MPSD, and SLD to return to the beacon at a set time, e.g., persons camping or in a store. Another way in which the beacon mode could be used would be for the holder of the designated beacon device to be able to actuate a "beacon signal" indicating to the holders of the other MCDs, MPSDs, and SLDs to come to the location of the designated beacon devise. For example, a chaperone for a teenager field trip could call the members of the group together when time to leave a given location.

Whereas there may be many embodiments of the present invention, each embodiment may meet one or more of the foregoing recited objects in any combination. It is not intended that each embodiment will necessarily meet each objective. Thus, having broadly outlined the more important features of the present invention in order that the detailed description thereof may be better understood, and that the present contribution to the art may be better appreciated, there are, of course, additional features of the present invention that will be described herein and will form a part of the subject matter of this specification.

BRIEF DESCRIPTION OF THE DRAWINGS

The accompanying drawings, which are incorporated in and constitute a part of this specification, illustrate embodiments and together with the description, serve to explain the principles of the methods and systems:

FIG. 1 is a block diagram depicting a communication system where a mobile device case is attached to a mobile device and a plurality of sensors is disposed remotely from the mobile device case.

FIG. 2 is a block diagram depicting a communication system where a mobile device case is attached to a mobile device and a plurality of sensors are coupled to the mobile device case.

FIG. 3 is a block diagram depicting a mobile device, a mobile device case, a plurality of sensors and the relationships between these components.

FIG. 4 is a block diagram depicting a mobile device, a mobile device case, a plurality of sensors coupled to the mobile device case and the relationships between these components.

FIG. 5 is a block diagram depicting two sets of mobile device and mobile device case, a plurality of sensors and the relationships between these components.

PARTS LIST

Figure 6:
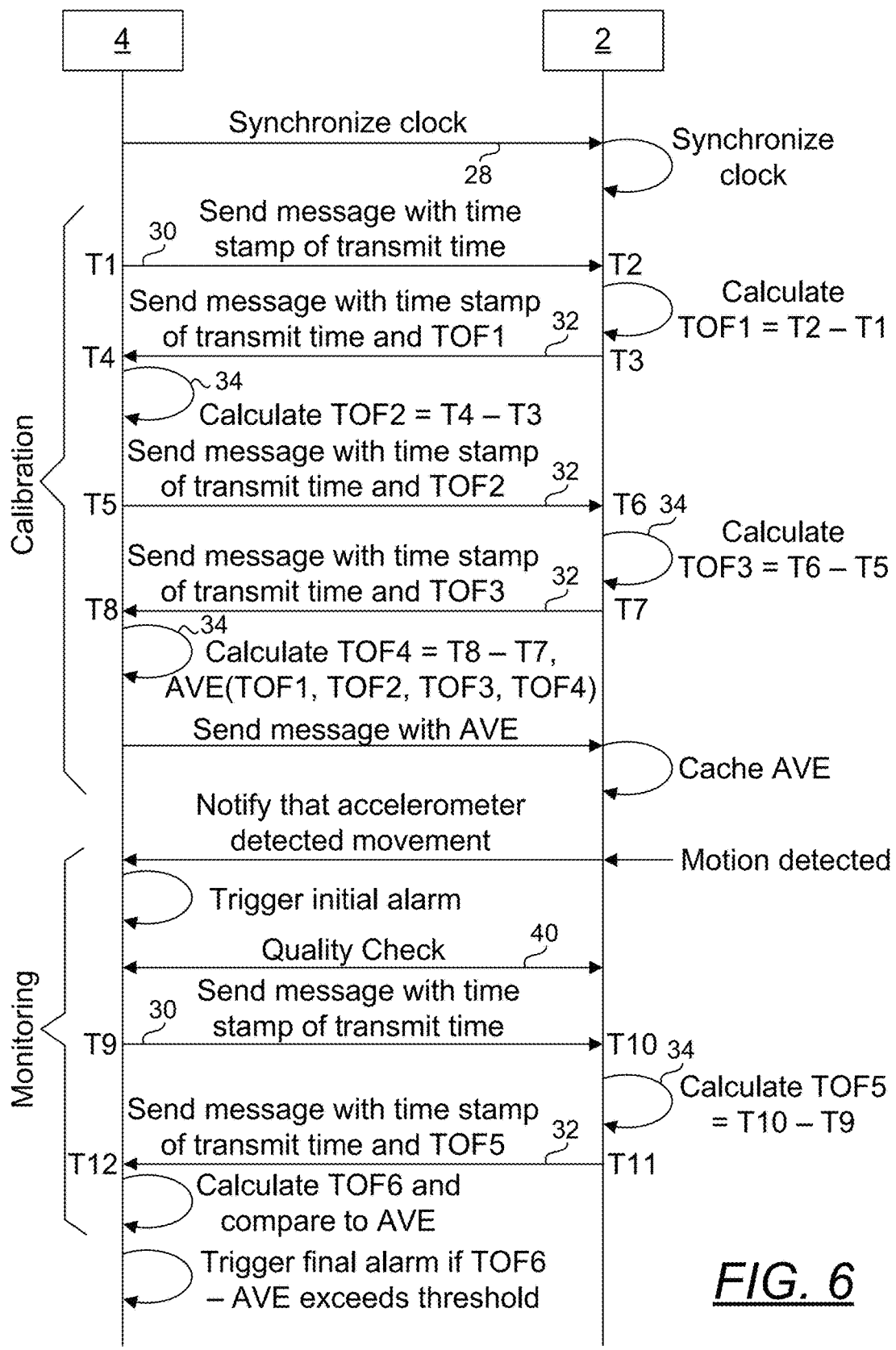
FIG. 6 is a sequence diagram depicting a means by which a mobile device case is used in conjunction with a mobile device to detect a movement of the mobile device case.

2—mobile device case
4—mobile device
5—socket
6—sensor
8—communication between mobile device case and sensor
10—communication between mobile device case and mobile device
12—communication between mobile device cases
14—communication between mobile devices
16—communication between mobile device and sensor
18—radius of trajectory of sensor C
20—distance between sensor A and mobile device case B
22—distance between mobile device case B and sensor C
24—total distance between sensor A and sensor C
26—communication between sensors
28—step of synchronizing clock time
30—step of sending message with time stamp of transmit time 32—step of sending message with time stamp of transmit time and calculated time of flight
34—step of calculating time of flight
36—plane
38—subgroup
40—quality check
42—first frequency originator device
44—second frequency originator device
46—broadcast signal having first frequency
48—broadcast signal having second frequency
50—frequency originator device, e.g., long range acoustic device (LRAD)
52—arc representing distance from frequency originator device
54—frequency receiver device, e.g., mobile device
56—first frequency receiver device
58—second frequency receiver device
60—distance between first frequency originator device and first frequency receiver device
62—distance between first frequency originator device and second frequency receiver device
64—distance between second frequency originator device and first frequency receiver device
66—distance between second frequency originator device and second frequency receiver device
68—distance between first and second frequency receiver devices on a mobile device
70—correction
72—axis connecting first and second frequency originator devices
74—information storage device
76—thigh
78—leg
80—femur
82—patella
84—tibia
86—fibula
88—break
90—sensor-equipped pill
92—receptacle
94—stomach
96—mouth
98—patient
100—protective shell
102—controller
104—transceiver
106—power supply
108—camera
110—memory Particular Advantages of the Invention The present system enables the use of a ubiquitous device, such as a mobile device, e.g., smart phone, in conjunction with a conveniently physically and functionally paired case, to function as a system to provide personal security and health monitoring, such as the determination of a situation requiring the user's attention.

The present localization system enables the use of a ubiquitous device, such as a mobile device, e.g., smart phone, in conjunction with a frequency originator device, which can be another ubiquitous device, such as a mobile device, e.g., smart phone. Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive, as claimed.

DETAILED DESCRIPTION OF A PREFERRED EMBODIMENT

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower). The terms "large motion" or "large movement" are used herein to mean a movement that is sufficient large, e.g., as a result of the opening or closing of a door, a position shift of about 5% per second, a position shift of at least about 1 inch per second, etc. A vibration caused by the operation of a common household appliance or air movement due to forced circulations in an indoor space shall not be considered to have the capability of causing a large motion or large movement (excluding some devices such as washing machines and clothes driers).

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. "Optional" or "optionally" means that the subsequently described event or circumstance may or may not occur, and that the description includes instances where said event or circumstance occurs and instances where it does not. Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the examples included therein and to the figures and their previous and following description.

FIG. 1 is a block diagram depicting a communication system where a mobile device case is attached to a mobile device 4 and a plurality of sensors 6 is disposed remotely from the mobile device case 2. The mobile device case 2 is physically and functionally coupled to the mobile device 4. In one embodiment, the mobile device case 2 is a cradle in which the mobile device is seated such that the mobile device case 2 provides protection against accidental impact, etc. The cradle is essentially a structure formed with a cavity that is shaped and sized substantially the same as the outside dimensions of at least a portion of the mobile device, e.g., the rear half of the mobile device or the portion of the mobile device facing away from a user while viewing a display of the mobile device such that the mobile device can be snuggly, securely and removably held. A mobile device case 2 is essentially a controller capable of communication with a mobile device 4 and one or more sensors 6. "Communication," as used herein is defined as communication via various communication means and protocols, e.g., Bluetooth, Global Positioning System (GPS), wireless local area network (Wi-Fi), etc. In one embodiment, an application capable of being installed in a mobile device is provided to cause the mobile device, via its transmitter and receiver, to communicate with a mobile device case 2 and a sensor 6. Each mobile device case 2 and sensor 6 may alternatively be equipped with a controller, transmitter and receiver to facilitate communication of one of these devices with another device. In one embodiment, a sensor 6 is an accelerometer between 2 g-8 g. In another embodiment, a sensor 6 is a 3-axis digital gyro with programmable full-scale ranges of about ±250, ±500, ±1000, and ±2000 degrees/sec (dps), which is useful for precision tracking of both fast and slow motions. In yet another embodiment, a sensor 6 is a low-power digital three dimensional (3D) magnetic sensor capable of measuring local magnetic fields up to about 10 Gauss with output data rates (ODR) up to 80 Hz. In one embodiment, a receiver is a device capable of receiving signals or messages transmitted as waves (e.g., radio and sound, etc.) having a frequency response falling within or outside that of the frequency response of a typical microphone which ranges from about 20 Hz to about 20 kHz.

FIG. 2 is a block diagram depicting a communication system where a mobile device case 2 is attached to a mobile device and a plurality of sensors 6 are coupled to the mobile device case 2. In one embodiment, a mobile device case 2 comprises a plurality of sensors 6. In the embodiment as shown in FIG. 2, a plurality of sockets 5 are made available on-board the mobile device case 2 and configured for receiving sensors 6. In use, only the necessary sensors 6 are inserted in the sockets and functionally connected to the mobile device case 2. Each socket is configured to functionally and physically receive a sensor such that the sensor can be securely seated in the socket, provide power to the sensor, ground the sensor and serves as a conduit for data communication between the sensor and the controller. Such a socket facilitates incorporation, removal or replacement of a sensor.

FIG. 3 is a block diagram depicting a mobile device 4, a mobile device case 2, a plurality of sensors 6 and the relationships between these components. The mobile device 4 is configured to communicate with the mobile device case 2 via communication 10 and each of the sensors 6 via communication 16. The mobile device case 2 is configured to communicate with each of the sensors 6 via communication 8. A mobile device case 2 may communicate with another mobile device case 2 via communication 12. A mobile device 4 may communicate with another mobile device 4 via communication 14. A sensor 26 may be configured to communicate with another sensor via communication 26. In one embodiment, the present system includes an application adapted to a mobile device 4 and at least one sensor 6. In another embodiment, the present system includes an application adapted to a mobile device 4, at least one mobile device case 2 and at least one sensor 6.

FIG. 4 is a block diagram depicting a mobile device 4, a mobile device case 2, a plurality of sensors 6 coupled to the mobile device case 2 and the relationships between these components. In one embodiment, the sensors communicates directly with the mobile device case 2 as if the sensors 6 are directly wired to the mobile device case 2 when the sensors are seated in the sockets of mobile device case 2. Each socket is functionally connected to the controller of a mobile device case 2 or sensor 6. In another embodiment, the sensors 6 communicate wirelessly to the mobile device case 2 as if the sensors are mounted wirelessly from the mobile device case 2.

FIG. 5 is a block diagram depicting two sets of mobile device 4 and mobile device case 2, a plurality of sensors 6 and the relationships between these components. This diagram is provided essentially to demonstrate that, in addition to communicating between dissimilar devices, communication may also occur between components of the same make, i.e., a mobile device 4 to another mobile device 4 and a mobile device case 2 to another mobile device case.

FIG. 6 is a sequence diagram depicting a means by which a mobile device case 2 is used in conjunction with a mobile device to detect a movement of the mobile device case 2. The system for carrying out such detection includes a mobile device case 2, a mobile device 4 and an accelerometer capable of detecting motion of the mobile device case 2. In this example, the mobile device case 2 is used to detect and verify a movement of the mobile device case 2 that is considered sufficiently severe to warrant an action to alert a user. The mobile device case 2 is attached to an object, the motion of which is to be detected while the mobile device 4 is placed in the vicinity the user such that the user can be alerted via an output of the mobile device 4. The mobile device 4 first initiates clock synchronization (step 28) with the mobile device case 2 by sending its clock time to the mobile device case 2. The time stamp at which the clock time starts to be transmitted is assumed to be the clock time. As it takes a finite amount of time for such transmission to be received at the mobile device case, the time at which such transmission to be received at the mobile device case 2 is no longer the clock time. The mobile device case thus sets its clock time with a time that corresponds to the clock time received and the duration for the clock time to be transmitted. Alternatively, the mobile device case 2 may initiate clock time synchronization. Upon synchronizing the clock of the mobile device case 2, the mobile device case 2 and the mobile device 4 are ready for a calibration process which involves averaging the time of flight of a message between the two devices 2, 4. The mobile device 4 initiates calibration by sending a message with the time stamp at which the message is started to be transmitted as in step 30. Upon receipt of the message, the mobile device case 2 then calculates (step 34) the time of flight of the message, i.e., the time it takes for the message to be transmitted from the mobile device 4 to the mobile device case 2 (time of flight). This is followed by a transmission from the mobile device case 2 which includes the time stamp at which a message started to be transmitted and the time of flight just calculated as shown in step 32. Upon receipt of the message, the mobile device 4 then calculates the time of flight of the message. The process of enabling the calculation of a time of flight by one device (by making available the time stamp of a transmission) in another device, the process of calculating the time of flight of a message by another device and the process of notifying another device of the time of flight is repeated until a satisfactory number of transmissions between the devices or until a satisfactory average of time of flight has been obtained. A satisfactory average of time of flight may be one which is tied to a satisfactory standard deviation. In this example, the calibration concludes with the averaging of four values of time of flight. The time of flight data is made available in both of the devices 2, 4. Alternatively, the time of flight and the average time of flight data may be retained in one of the two devices and the average time of flight data is only made available to the device which requires it. After the time of flight has been calculated, the mobile device case 2 is now ready to detect motion.

In order to eliminate false detection, the system must detect a motion warranting a response from the user in conjunction with the time of flight data indicating a distance change has occurred. A triggering of the accelerometer signals that a motion has been detected and a notification is sent from the mobile device case 2 to the mobile device 4. This event marks the start of the monitoring phase of the sequence. An initial alarm may be emitted to the user signaling the detection a motion has been detected in the mobile device case 2. Alternatively, the monitoring phase may start immediately after clock synchronization has completed. Upon detecting a motion with the accelerometer, a question remains as to whether or not the motion is caused by an action which warrants a response at either the mobile device 4 or the mobile device case 2. Upon receiving the notification from the mobile device case 2, the mobile device 4 initiates a process where one or more values of the time of flight are obtained. The process in getting a time of flight value is similar to the process in which a time of flight value is calculated in the calibration process. As the time of flight of a message corresponds the distance between the mobile device case 2 and the mobile device 4, a movement in the mobile device case 2 causes the time of flight of a message transmitted between the two changes. Therefore, a significant deviation of the time of flight from the average time of flight previously established in the calibration process may signal a large change in the position of the mobile device case 2 and an alarm may be triggered at the mobile device 4 to indicate such event. If an additional device, such as a sensor 6 or a mobile device case 2 were to be added to the network, clock synchronization may be performed to the entire network or to the newly added device alone. A request for clock synchronization may be initiated via the device to be added. In one embodiment, such request is actuated via a button functionally connected to such request. Although the example depicted in FIG. 6 includes a mesh network of a mobile device case 2 and a mobile device 4, two or more mobile devices 4 may be used in place of the combination of a mobile device case 2 and a mobile device 4. In general, the type of clock time synchronization is selected based on the proximity of the devices involved to each other. In an embodiment where devices are disposed in close proximity, mobile devices are synchronized via a peer-to-peer mechanism. A peer-to-peer mechanism includes, but not limited to, the use of a Near Field Communication (NFC), Bluetooth or Wi-Fi, etc. transmit-receive pair to transmit the clock time and transmit time of a first mobile device to a second mobile device where its clock is reconciled with the clock time of the first mobile device. In an embodiment where devices are disposed apart at great distances, mobile devices clock time synchronization may be synchronized via a web server. The clock time and transmit time of a first mobile device are transmitted via a web connection to a second mobile device where its clock is reconciled with the clock time of the first mobile device. A web server may be accessed via a mobile device wirelessly or by hard wire.

In order to determine to a high degree of certainty that a large motion has indeed occurred, a quality check 40 including the following two quality checks may be performed.

An Example of a Quality Check for Confirming that a Movement has Begun

Just after the initial distance between devices is determined (first measurement after any calibration loop), the device can be disposed in a stand-by mode to conserve power. If the accelerometer detects a movement while in standby mode, the device having the accelerometer wakes up and starts to send time data such that time of flight (TOF) data can be calculated in the device receiving the time data. The accelerometer serves here to both provide a confirmation of movement and allow for a power conserving stand-by mode. In the event that environmental factors may give difficult signal readings (e.g., moving steel objects that could cause signal reflections that could falsely be interpreted as movement), such quality check can reduce extraneous or unreliable time data. The use of a standby mode allows for less power usage by only making transmissions when movement begins. It is important to note here that both devices in a two device system of a phone and a sensor could use sleep mode, but TOF calculations need to begin if either one of the two begins to move.

Examples of a Quality Check for when Devices are in Motion and are Regularly Making TOF Calculations Scenario A: Accelerometers in both devices compare relative speed to each other.

Scenario B: Gyros in both devices compare relative angle of movement off of horizontal between both devices.

Scenario C: Compasses in both devices compare relative directional heading between both devices.

Scenarios A, B, and C contribute to helping to maintain good relative position between devices while TOF method continues to establish relative distance, especially for use when viewed on a mobile device screen with a grid reference. Note that compass and gyro are used only to assist in orientation as in quality check and they are used for screen display/interface and do not detract from TOF.

Figure 7:
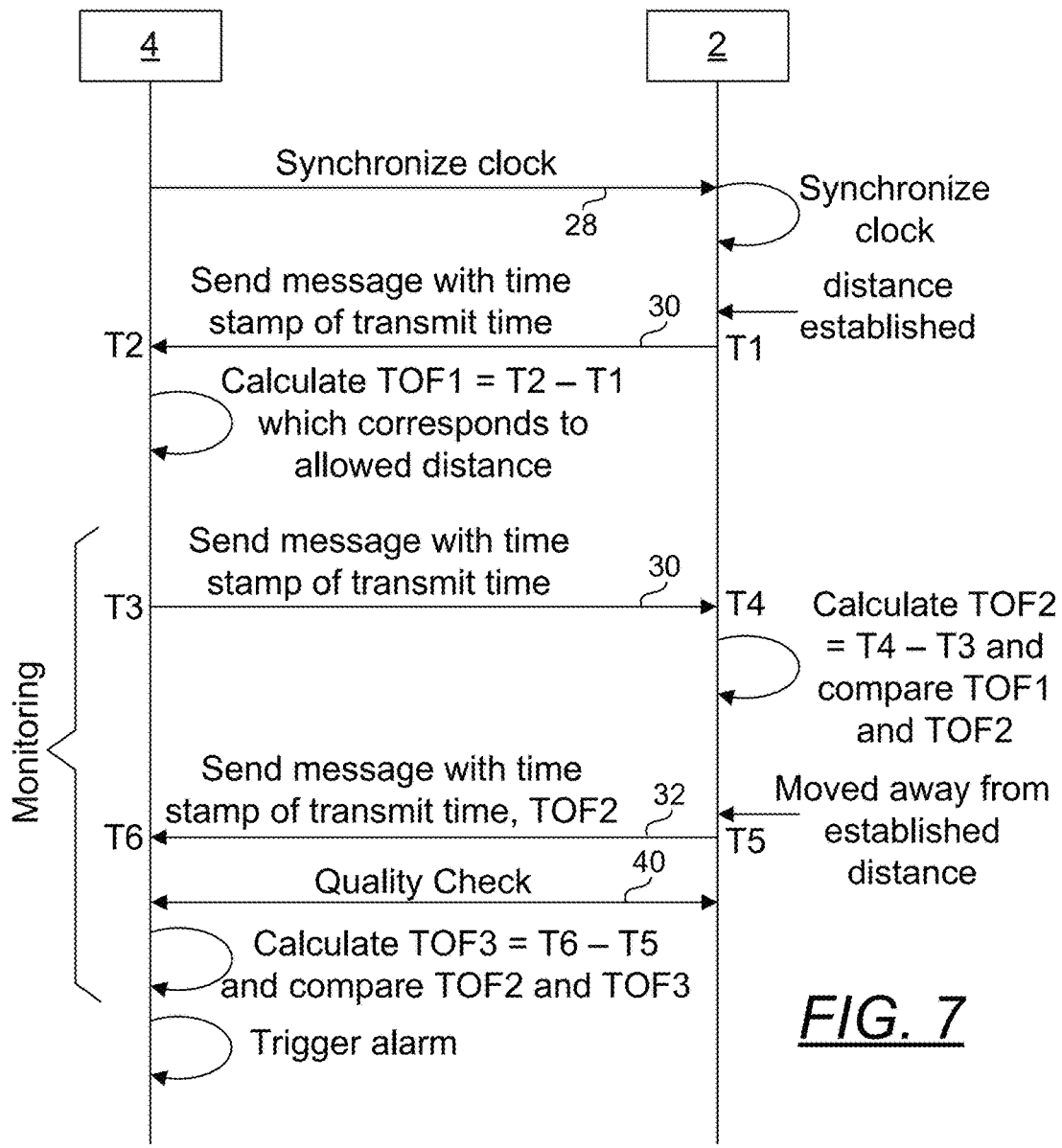
FIG. 7 is a sequence diagram depicting a means by which a mobile device case is used in conjunction with a mobile device to detect a condition where the distance between the two devices has grown beyond a predetermined threshold.

FIG. 7 is a sequence diagram depicting a means by which a mobile device case 2 is used in conjunction with a mobile device 4 to detect a case where the distance between the two devices 2, 4 has grown beyond a predetermined threshold. In one aspect, an individual to be monitored is given the mobile device case 2 while an individual monitoring the mobile device case 2 uses the mobile device 4. Again, the clocks of the two devices 2, 4 are first synchronized. Upon synchronizing the clocks in the two devices 2, 4, the devices enter a monitoring phase. Prior to the monitoring phase, a time of flight corresponding to the maximum distance allowed between the two devices must first be established. At the start of the monitoring phase, the mobile device case 2 initiates communication by sending a message with the time stamp at which the message is started to be transmitted as in step 30. Upon receipt of the message, the mobile device 4 then calculates the time of flight of the message, i.e., the time it takes to the message to be transmitted from the mobile device 4 to the mobile device case 2 (time of flight). This is followed by a transmission from the mobile device case 2 which includes the time stamp at which a message starts to be transmitted and the time of flight just calculated as shown in step 32. Upon receipt of the message, the mobile device 4 then calculates the time of flight of the message and the present time of flight is compared to the previously calculated time of flight. For simplicity, the present diagram shows only two sets of time of flight. In practice, many more sets of time of flight are obtained and analyzed. If a large discrepancy between the two values (which indicates a departure of a device from another) has been detected, an alarm may be activated to indicate such an event.

Figure 8:
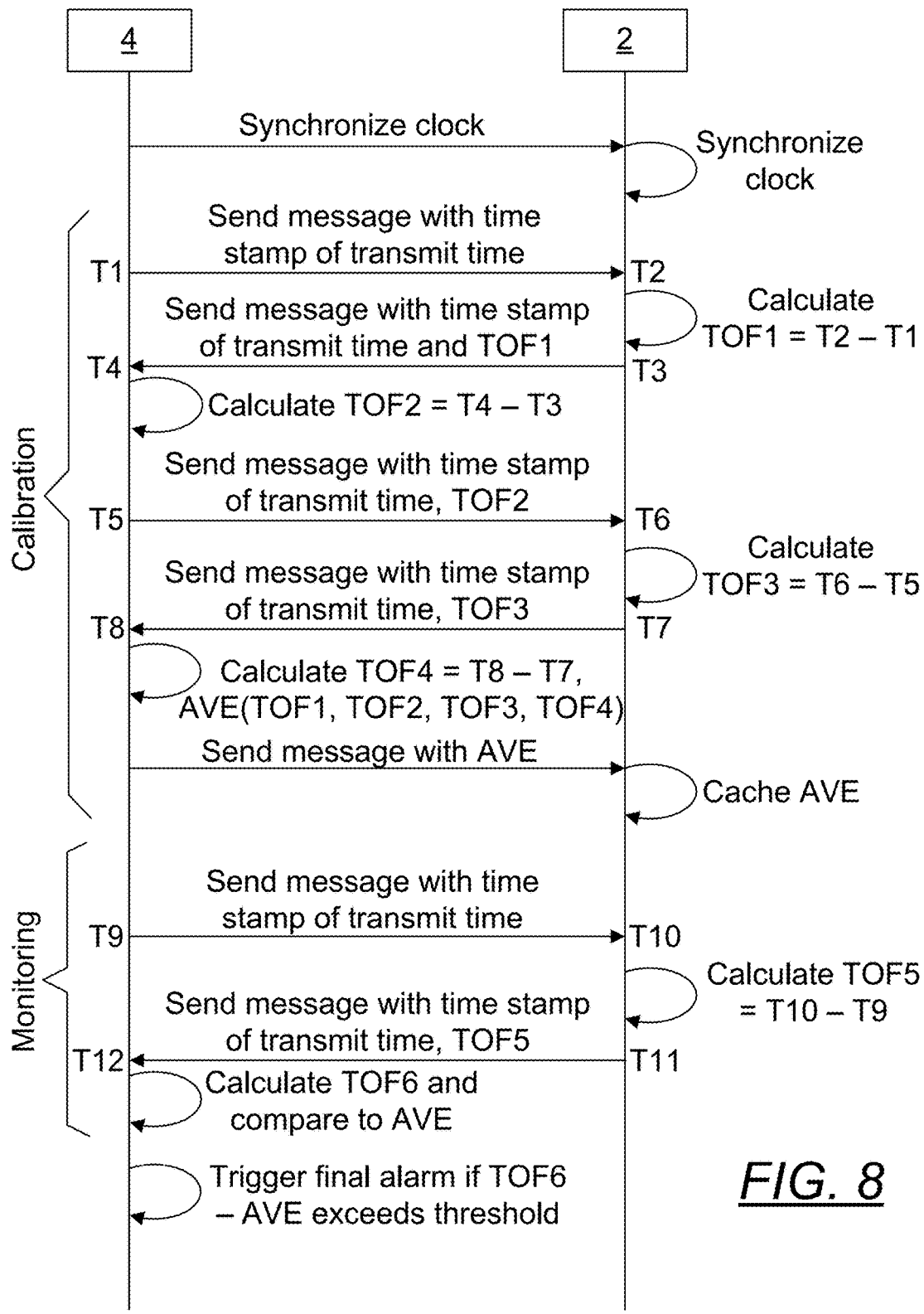
FIG. 8 is a sequence diagram depicting a means by which a mobile device case is used in conjunction with a mobile device to detect an intrusion in a space between the two devices.

FIG. 8 is a sequence diagram depicting a means by which a mobile device case 2 is used in conjunction with a mobile device 4 to detect an intrusion in a space between the two devices. The two devices 2, 4 are spread apart a distance such that a space (between the two devices) in which an intrusion is to be detected is formed. Similar to the scenario of FIG. 6, the two devices are clock synchronized and calibrated. The main difference between the present scenario and the one shown in FIG. 6 lies in the lack of an accelerometer in the present scenario. An intrusion in the space comes as a disturbance or a change to values of the sets of time of flight. If a present time of flight value varies significantly from the previous time of flight value, an intrusion is said to have been detected. In another embodiment, the present system seeks the entry of a new, unknown signal into its monitored area (e.g., various types of signals such as transmissions from the phone of an intruder or the signal of a remote control device). It should be noted that the system may also use changes in the time of flight of signals to detect if there is movement in the room that does not cause a sensor to move.

Figure 9:
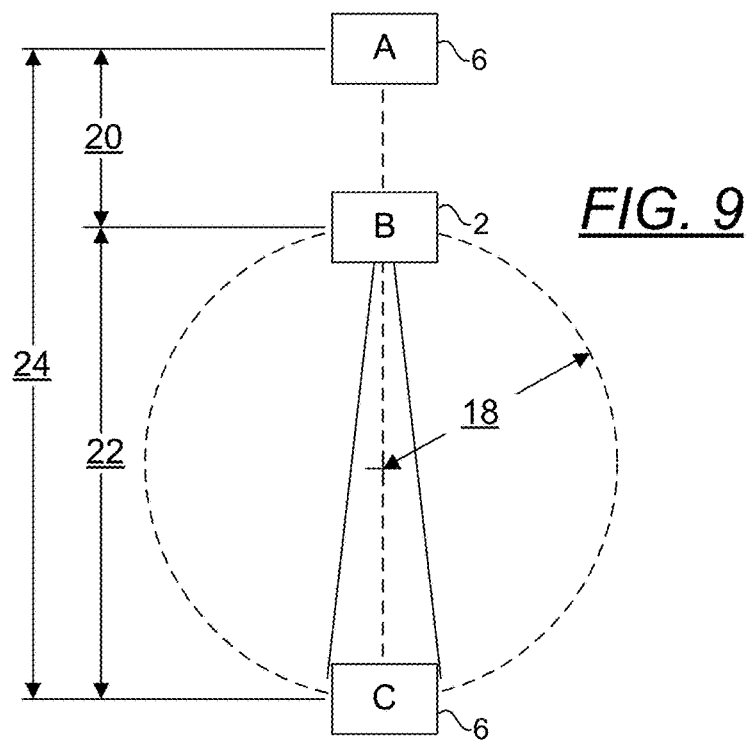
FIG. 9 is a diagram depicting an example of the use of a mesh network for communication between multiple devices or detection of one or more devices in a network.

FIG. 9 is a diagram depicting an example of the use of mesh network for communication between multiple devices or detection of one or more devices in a network. In this example, sensor A and mobile device case B are disposed at fixed locations at distance 20 apart and sensor C is mounted to an object configured to travel in a circular trajectory as shown in FIG. 9. The mobile device case B includes a directional antenna configured to detect an object in a direction coaxial to the direction from sensor A to mobile device case B. It is assumed that sensor A is not capable of directly detecting sensor C or providing a distance measurement between sensor A and sensor C, due to an obstruction or not having the same method of communication. It is further assumed that when sensor C comes within the field of view of the directional antenna, the mobile device case 2 will be capable of detecting the presence of sensor C. Therefore, although sensor A is not capable of detecting the presence of sensor C in the mesh network depicted in FIG. 9, the mobile device case 2 may relay location of sensor C relative to sensor A to sensor A if the radius 18 of sensor C trajectory is known. For example, in the positions shown, sensor A is disposed at a total distance 24 of distances 20 and 22. Distance 22 is twice radius 18. In an embodiment not shown, the mobile device case B may be replaced with a mobile device having a built-in antennae.

Figure 10:
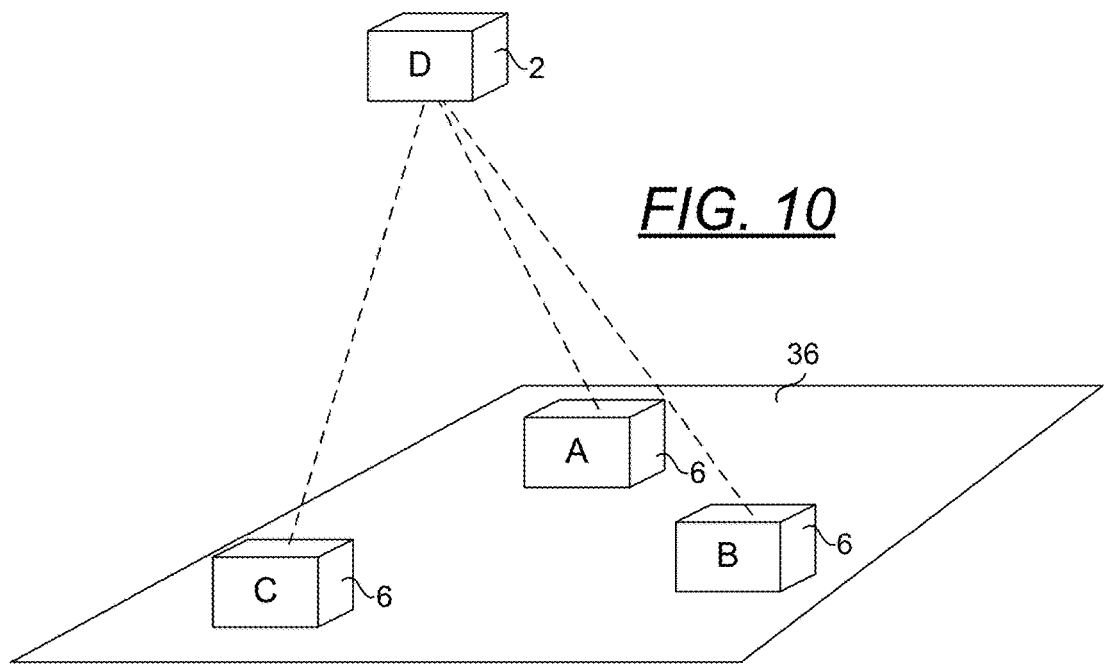
FIG. 10 is a diagram depicting an example of the use of a mesh network for locating a device.

FIG. 10 is a diagram depicting an example of the use of a mesh network for locating a device. In this example, sensors A, B and C are disposed at fixed known locations substantially upon a floor 36. The location of the mobile device case D, in relation to the sensors A, B and C, is to be determined by triangulation. Distances D-C, D-A and D-B are estimated based on the time of flight of signals communicated between each of the sensors A, B and C and the mobile device case 2. As there are two possible solutions, by placing the sensors A, B and C on the floor 36, the location of the mobile device case D relative to the sensors A, B and C can be estimated. The possible location of mobile device case D "under" the floor 36 as the other solution can be eliminated. Sensors A, B and C may alternatively be disposed at any location and not on a floor. If the signals communicated between the devices could travel through a floor, the strength of the signals may provide clue as to the proper solution as weak/problematic signals may indicate the second solution "under" the floor.

Figure 11:
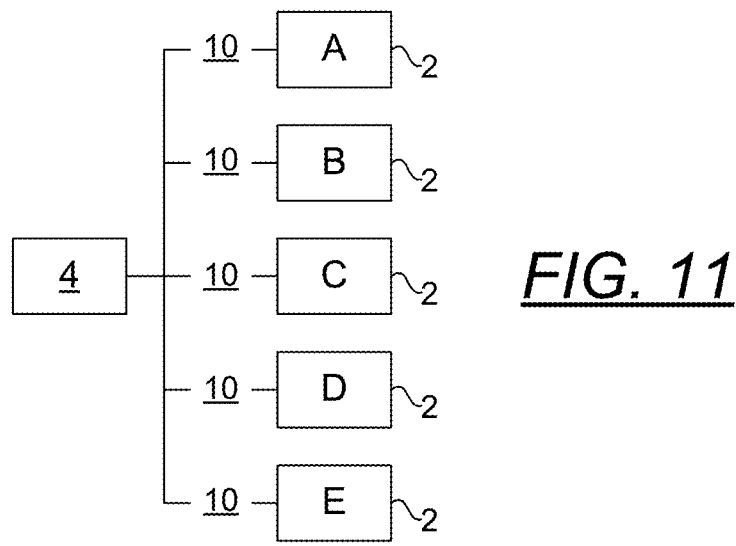
FIG. 11 is a block diagram depicting a mobile device, a plurality of mobile device cases and the relationships between these components.
Figure 12:
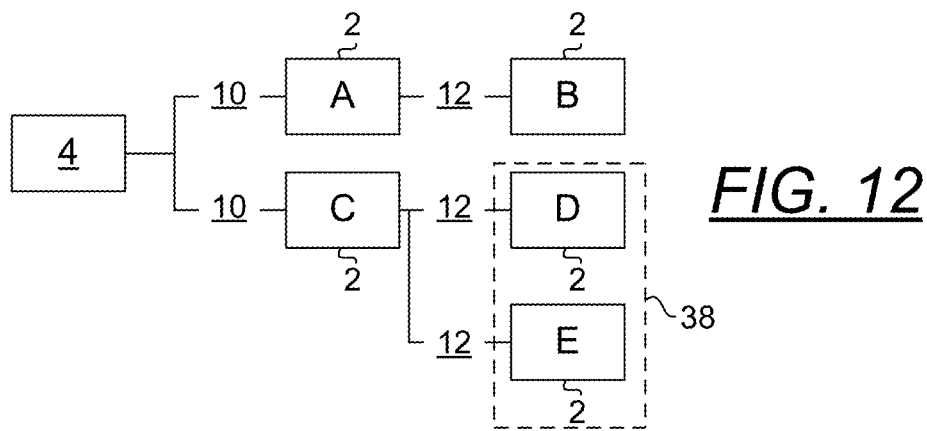
FIG. 12 is a block diagram depicting the components of FIG. 11 and functional connections between these components that are different than those disclosed in FIG. 11.
Figure 13:
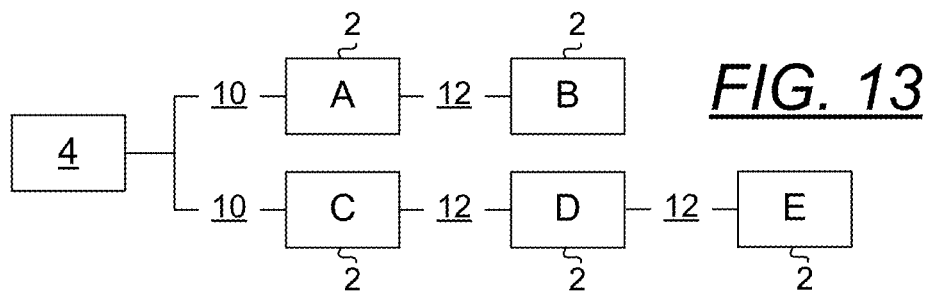
FIG. 13 is a block diagram depicting the components of FIG. 11 and functional connections between these components that are different than those disclosed in FIG. 11.

FIG. 11 is a block diagram depicting a mobile device 4, a plurality of mobile device cases and the relationships between these components. Each of the mobile device cases 2 is functionally connected directly to the mobile device 4. FIG. 12 is a block diagram depicting the components of FIG. 11 and functional connections between these components that are different than those disclosed in FIG. 11. In this mesh network, each of mobile device cases A and C is functionally connected directly to the mobile device 4. Mobile device case B is functionally connected to another mobile device case, i.e., mobile device case A. Each of mobile device cases D and E is functionally connected to another mobile device case, i.e., mobile device case C. In one aspect, it is possible to extend the range between mobile device 4 and a mobile device case 2 by functionally indirectly connecting a mobile device case (such as mobile device cases B, D and E) to the mobile device 4. In another aspect, mobile device cases 2 may alternatively be functionally grouped into one or more subgroups 38. A subgroup 38 can be viewed as a group where its constituents (e.g., mobile device cases D and E) functionally cooperate to yield a result that can then be relayed through at least one of the constituents to another component in the mesh network, e.g., the mobile device 4. For instance, if each of the mobile device cases D and E is equipped to take temperature readings, mobile device cases D and E may be configured to provide an average temperature reading based on the readings of mobile device cases D and E. FIG. 13 is a block diagram depicting the components of FIG. 11 and functional connections between these components that are different than those disclosed in FIG. 11. FIG. 13 depicts another possible means of forming a mesh network. In this example, mobile device case E is functionally connected to mobile device case D. In one embodiment, a subgroup is formed by bringing two components within the sphere of influence of each other and using a trigger, e.g., a button press to cause such relationship to be established. In another embodiment, a subgroup is formed by bringing components within the sphere of influence of each other such that a list of components present within the sphere of influence is visually presented and a selection can be made as to the components that form a subgroup.

Alternatively, the mobile device cases 2 of the examples depicted in FIGS. 11-13 may be replaced with sensors 6 and a mobile device case 2 may be used in place of the mobile device 4.

Figure 14:
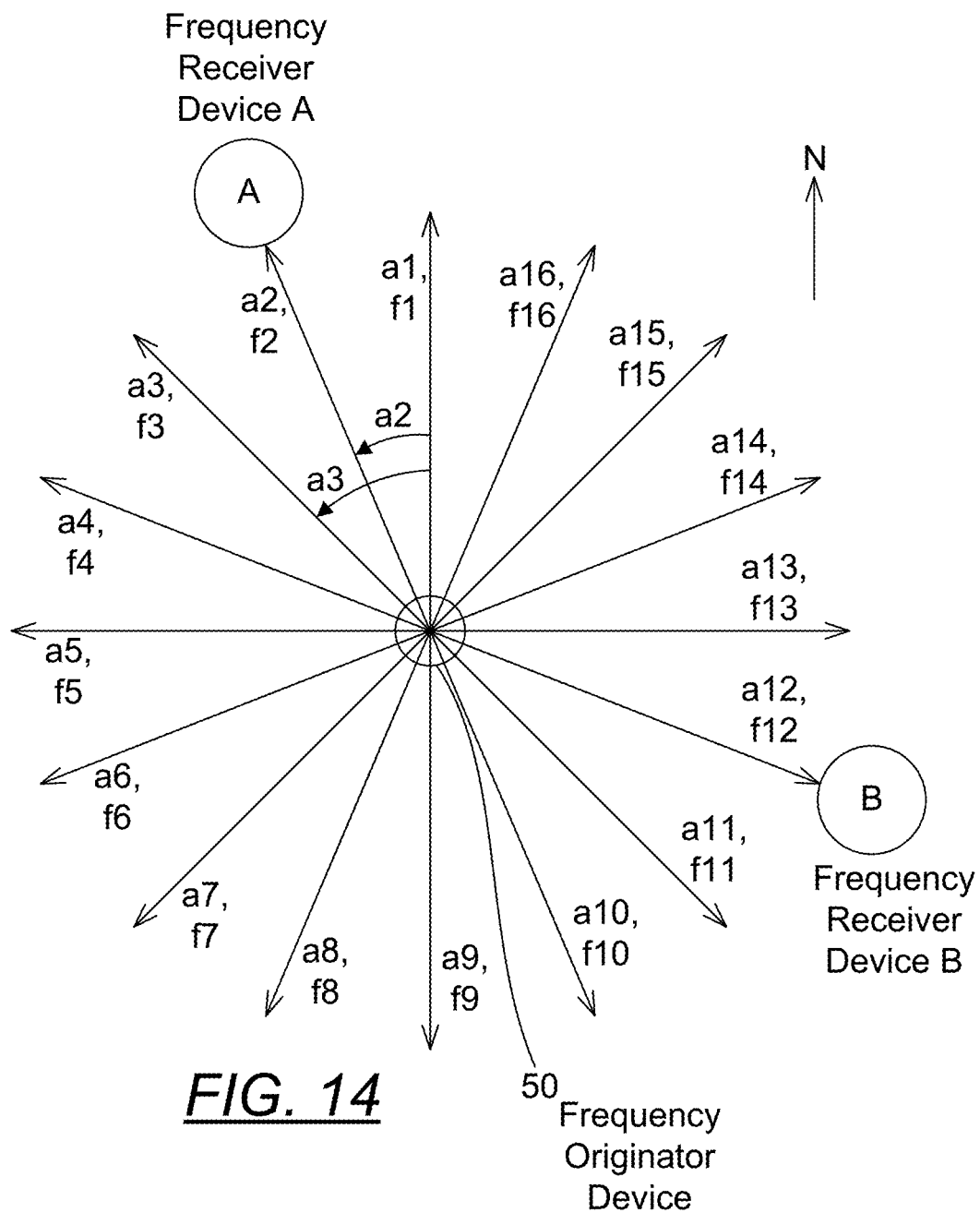
FIG. 14 is a diagram depicting one embodiment of a present localization system.

FIG. 14 is a diagram depicting one embodiment of a present localization system. In this embodiment, the location determination of a frequency receiver device (e.g., device A or B) is made based on the direction at which a signal or message is received from a frequency originator device. A frequency receiver device disclosed herein can be a mobile device already equipped with an on-board or built-in or external microphone, a device capable of receiving signals or messages transmitted as waves having a frequency response falling within or outside that of the frequency response of a typical microphone which ranges from about 20 Hz to about 20 kHz. A frequency receiver device which is said to have a frequency response of the typical range of frequencies can reproduce all frequencies within this range but not outside of this range. A frequency receiver device capable of a frequency response outside that of this range is adapted to reproduce frequencies outside of this range. A frequency originator device disclosed herein can be a broadcaster or any devices adapted to transmit signals or messages in waves having a frequency. In one embodiment, the frequency originator device 50 is a long range acoustic device (LRAD) which can be configured to broadcast signals of various frequencies at various orientations. In another embodiment, a phased array speaker system is used as the frequency originator device. Referring back to FIG. 14, at orientation a2, a signal having a frequency of f2 is broadcasted from LRAD. At orientation a12, a signal having a frequency of f12 is broadcasted from LRAD. Other signals of various other frequencies are broadcasted at their respective frequencies. At its depicted location, mobile device A (a frequency receiver device) is disposed at a location for receiving a signal at orientation a2 of frequency f2. In practice, LRAD can be a wave emitting device that is mounted on a rotary table such that it may be configured to emit signals of various frequencies at high speed depending on its orientation about its axis of rotation. Alternatively, multiple wave emitting devices may be disposed at different orientations instead, each configured to emit signals at a fixed frequency and pointed outwardly from a center. The latter is more robust as any delays due to the physical rotation of the wave emitting device as in the former will not occur. Each frequency originator device is programmed to emit a message in the direction the frequency originator device is disposed. Each message is therefore referred to as a directional message as only a frequency receiver device positioned within the field of influence of the directional message can receive this directional message.

In this embodiment, the cost of operating both the frequency originator device and the frequency receiver device is minimal. Most of the energy consumption of the present system lies in the broadcast of signals from the frequency originator device. When compared to a conventional localization device, e.g., a GPS system which not only requires external signals, e.g., those of satellites and relay stations but also may succumb to inclement weather, the present localization system utilizes smaller amounts of resources. There is neither satellite infrastructure nor any third party fees required in the present systems. The present systems are self-contained system without requiring external fees for signal information, e.g., GPS. The present systems can be readily used at low costs as they utilize existing communication means in sending alarms or danger notices, e.g., over an internet, data, or text, connection that would already be a part of the mobile device owners services. In the present systems, additional monitoring fees are not required to notify the authorities as the systems that can directly call the police through the mobile device, e.g., mobile phone. The energy consumption in the frequency receiver device is minimal as compared to other means of localization. The present systems utilize low energy consuming technology, e.g., sound frequencies and as a result, the devices in the systems do not need to be powered by large amounts of on-board battery power, reducing the battery costs which constitute a significant total cost portion in any mobile device. As the present systems are readily movable, they can travel easily with their owner from one location to another, relieving the need for multiple systems at multiple locations. In any systems disclosed herein, a speaker that is built-in or external to a mobile device can be used as a frequency originator device while a microphone that is built-in or external to the mobile device can be used as a frequency receiver device. As these components are typically already bundled with a mobile device, e.g., cell phone, no additional equipment or costs are required. In terms of the processors of the present systems, high volume or mass produced mobile devices such as a cell phone or tablet, etc., are readily equipped with such parts.

Although a cell phone or tablet is used for other purposes, such as personal communication, etc., a cell phone or tablet is available at a much lower cost than a lower volume central processing unit for a security system due to economy of scale in the case of the cell phone or tablet. Compared to existing localization systems designed primarily for use in an outdoor, unobstructed environment, the present systems function by utilizing signals coming from devices already in the system or that have traveled together at the same time into an enclosed location. The present systems therefore do not rely on an existing infrastructure in the building to provide a signal source or data (e.g., they do not rely on a Wi-Fi being present).

In determining the location of a frequency receiver device with respect to a frequency originator device of a known location, the following steps are taken. First, the distance between the frequency receiver device and the frequency originator device is determined. In one embodiment, this is achieved by first synchronizing a clock of the frequency originator device with a clock of the frequency originator device. Then a directional message containing a broadcast time at which the directional message is broadcasted from the frequency originator device at an orientation about an axis of rotation of the frequency originator device and received by the frequency receiver device. The time of flight of the directional message is obtained by calculating the difference between a receive time at which the directional message is received by the frequency receiver device and the broadcast time. The distance between the frequency originator device and the frequency receiver device is determined by multiplying the time of flight of the directional message by the speed of the directional message. This is followed by determining the frequency of the directional message and determining the orientation of the directional message with respect to the frequency originator device by looking up a table containing orientations of messages about the frequency originator device with respect to the frequency of the messages. The location of the frequency receiver device can then be calculated based on the orientation of the directional message and the known location of the frequency originator device. It shall be noted that the known location is movable. In other words, it is the relative positioning of the frequency receiver device and the frequency originator device that is important. For example, in an application where a frequency receiver device is configured to follow a frequency originator device at a distance, the frequency originator device may be in a moving state at all times, but the frequency receiver device must move with the frequency originator device to maintain a preprogrammed distance.

Figure 15:
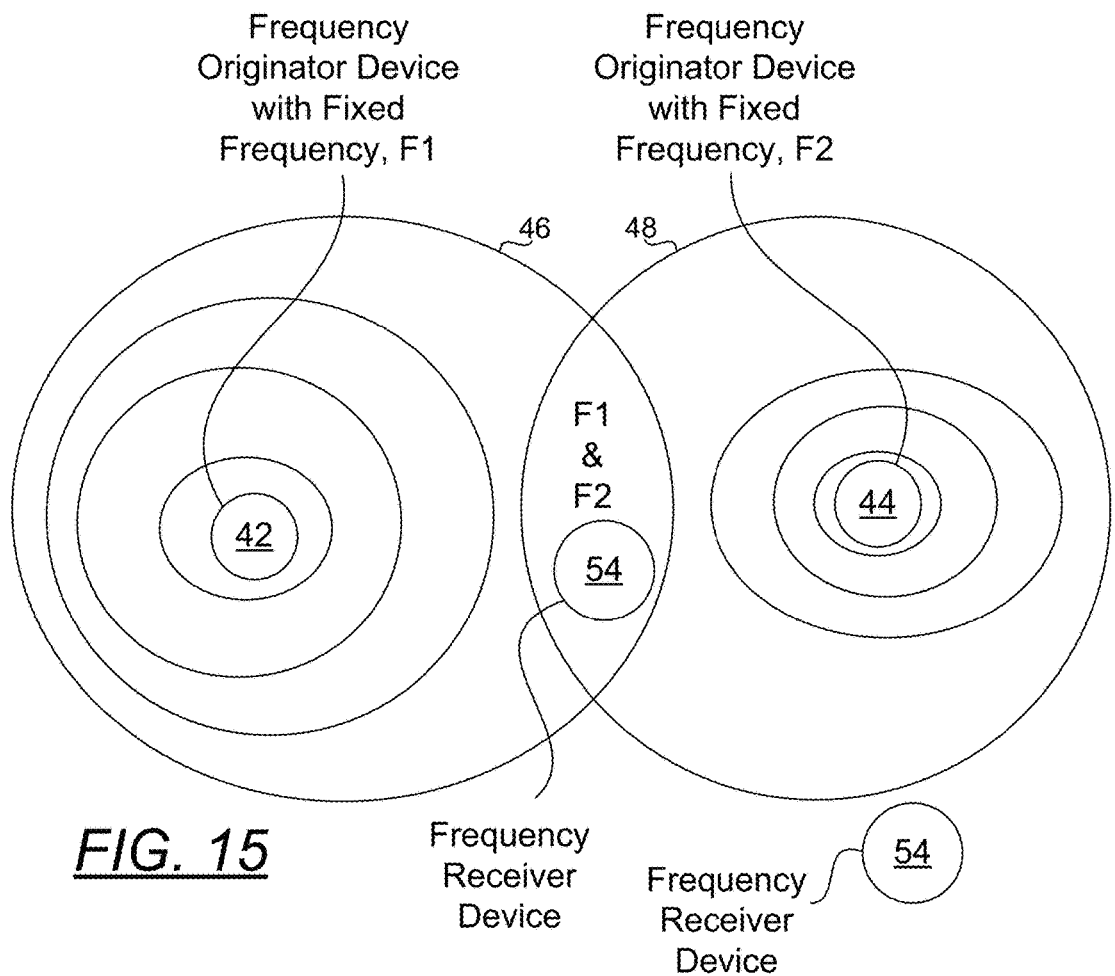
FIG. 15 is a diagram depicting another embodiment of a present localization system.
Figure 16:
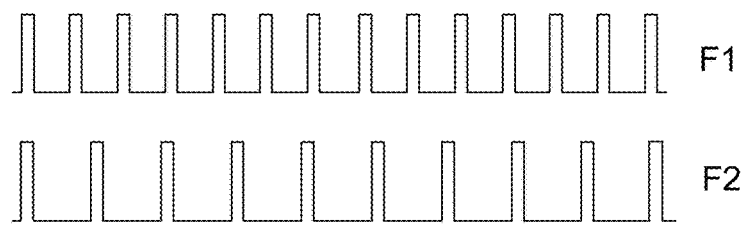
FIG. 16 is a diagram showing two different frequencies broadcasted using two different frequency originator devices as shown in FIG. 15.
Figure 17:
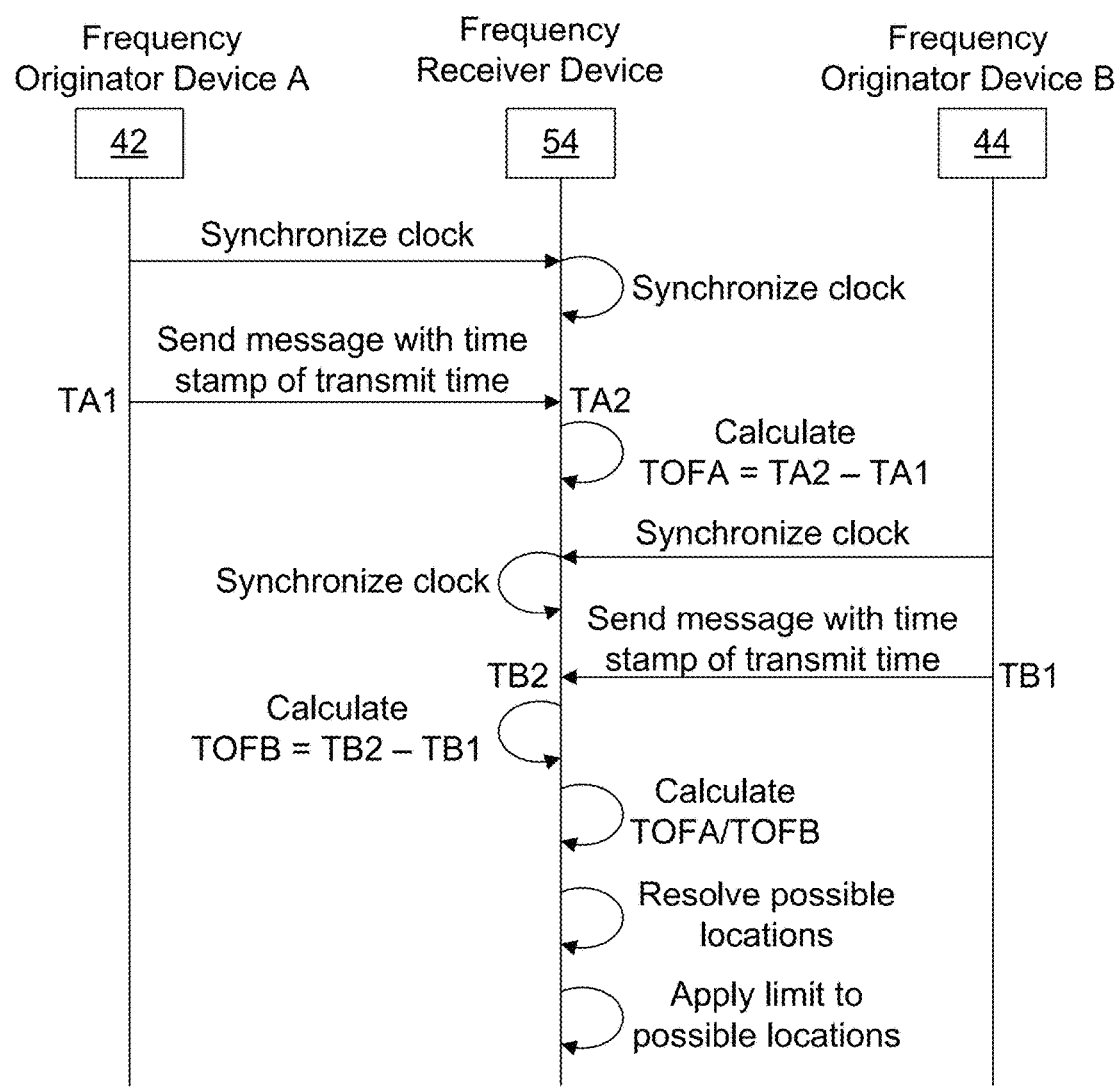
FIG. 17 is a sequence diagram depicting a means by which a device may be localized.
Figure 18:
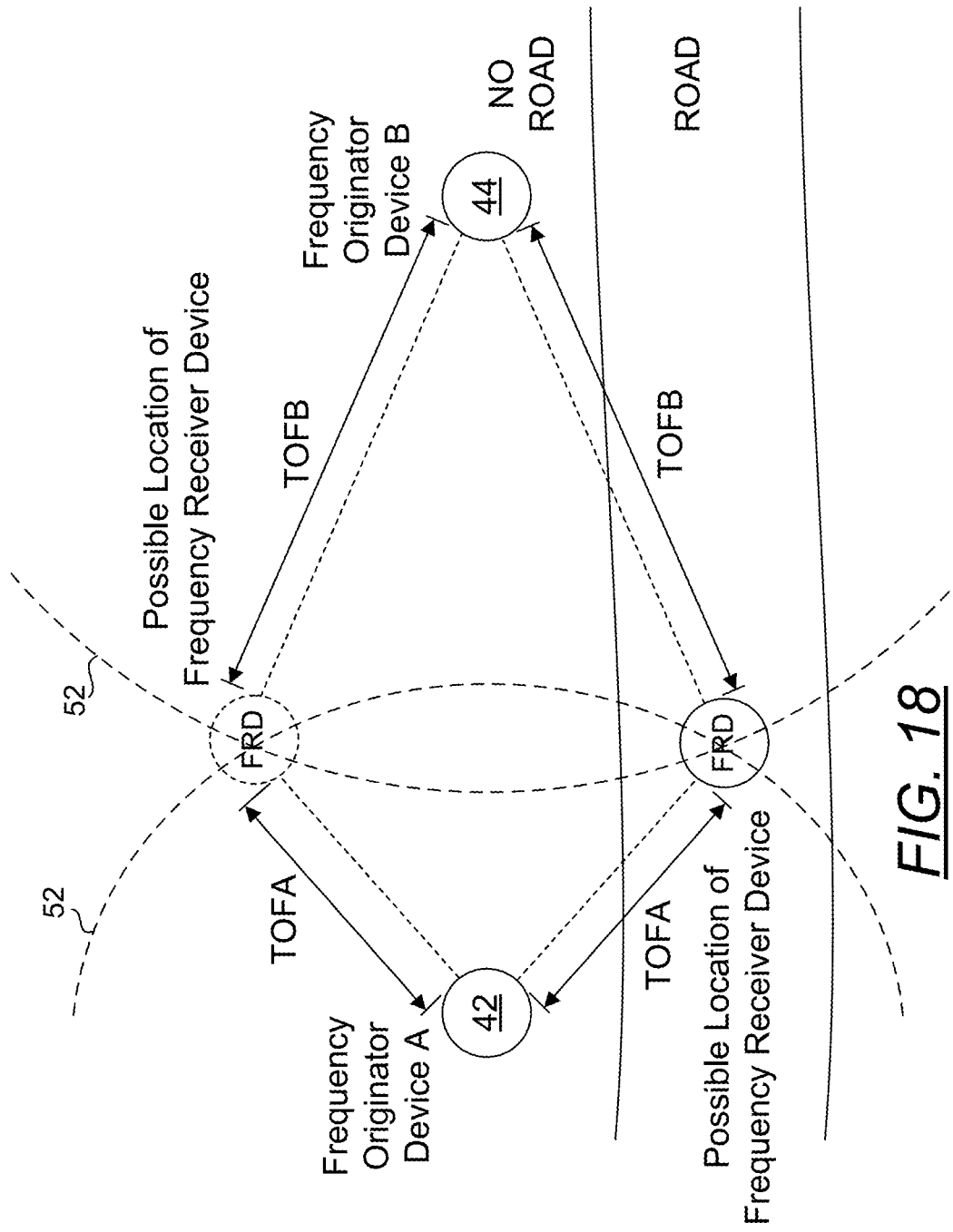
FIG. 18 is a plan view depicting a means by which localization is perfected with additional information.

FIG. 15 is a diagram depicting another embodiment of a present localization system. In this embodiment, two non-directional frequency originator devices are provided, each used to broadcast a signal or message having a fixed frequency, F1 or F2. FIG. 16 is a diagram showing signals or messages of two different frequencies broadcasted using two different frequency originator devices as shown in FIG. 16. Note the difference in wavelengths between the two messages. FIG. 17 is a sequence diagram depicting a means by which a device may be localized. FIG. 18 is a plan view depicting a means by which localization is perfected with additional information. In a two-dimensional space, a frequency receiver device may be said to assume one of the two possible locations as shown in FIG. 15. Referring to FIG. 18 and upon determining the distance of a frequency receiver device 54 from a frequency originator device using a method disclosed elsewhere herein, an arc 52 representing points equidistant from a frequency originator device can be disposed about the frequency originator device. In a two dimensional space, there exists two intersecting points, each representing a possible location of the frequency receiver device. In practice, a look-up table of the relative position of the frequency receiver device with respect to the ratio of the time of flight of messages 46, 48 (TOFA/TOFB) can be used to reduce real time computations in one or more controllers, e.g., one disposed in the frequency receiver device or one or both of the frequency originator devices of the localization system in resolving the location of the frequency receiver device given the locations of the frequency originator devices A and B. TOFA and TOFB represent the time of flight corresponding to the distances between the frequency receiver device and the frequency originator device A 42 and B 44, respectively.

The following steps are taken in determining the location of a frequency receiver device with respect to at least two frequency originator devices where the location of each is known. In the embodiment shown in FIG. 17, this is achieved by first synchronizing a clock of the frequency receiver device with a clock of one of the at least two frequency receiver devices. This is followed by receiving by the frequency receiver device, a message containing a broadcast time at which the message is broadcasted from the frequency originator device. Then a time of flight of the message is obtained by calculating the difference between a receive time at which the message is received by the frequency receiver device and the broadcast time. The above steps are repeated with a second frequency receiver device to result in a first time of flight, TOFA and a second time of flight, TOFB. A ratio of TOFA and TOFB is then calculated. Possible locations of the frequency receiver device are then resolved by looking up a table containing possible locations of the frequency receiver device with respect to the ratio of the first and second time of flight. The table is essentially a look-up table listing the TOFA/TOFB ratio with respect to the locations of the frequency receiver device relative to the locations of the frequency originator devices. As there are two possible solutions or locations in each two dimensional space as shown in FIG. 18, additional information is required to rule out one of the possible locations. At least one limit is applied to the possible locations to select one of the possible locations with high certainty. In the example shown in FIG. 18, frequency originator devices A and B are overlaid atop a map depicting a road. In this example, as it is assumed that the frequency receiver device is used for road navigation, the applied assumption or limit results in a plausible solution which points to the location of the frequency receiver device disposed on a road instead of a location where no roads exist. In another embodiment, the limit includes the time of flight results obtained from a third frequency originator device in a similar manner as in the case of the other two frequency originator devices. In this case, a unique solution exists which is disposed at a measured distance (or its corresponding time of flight) from frequency originator device A, a measured distance (or its corresponding time of flight) from frequency originator device B and a measured distance (or its corresponding time of flight) from the third frequency originator device in a two dimensional space. In order to obtain a unique solution in a three-dimensional space, a fourth frequency originator device will be required. In another embodiment, the limit includes the magnetization of a magnetic material, e.g., a ferromagnet, and the strength and/or direction of the magnetic field at a point in space as indicated by a magnetometer. The frequency originator devices may also be movable provided that the positional relationships between the frequency originator devices are known.

A frequency originator device can be a mobile device and whenever possible, it is preferably connected to a wall power source such that its service is uninterrupted. A frequency receiver device is preferably a mobile device such that its use is not tethered to a fixed location. The present localization method may be extended for use with venues already having frequency originator devices, e.g., stadiums, subways, malls, parking lots, etc.

Interference may occur during transmission of data from one device to another. In order to avoid interference, a strategy that determines the most favorable frequency of a signal is used. In doing so, signals are transmitted at varying frequencies from a frequency originator device to a frequency receiver device at, e.g., regular intervals. The signal with the shortest time of flight is considered to be the signal having most suitable signal frequency as signals received at a longer time of flight may indicate the presence of echoes or other effects of interference. Upon determining the most suitable signal frequency, future communications between the frequency originator device and the frequency receiver device will then be made at this frequency to avoid interferences.

The present systems are also capable of use underwater where GPS is unavailable. When used underwater, suitable water-proofing technologies shall be used to ensure readily available mobile devices which are typically designed for use in air do not get water intrusions.

Figure 19:
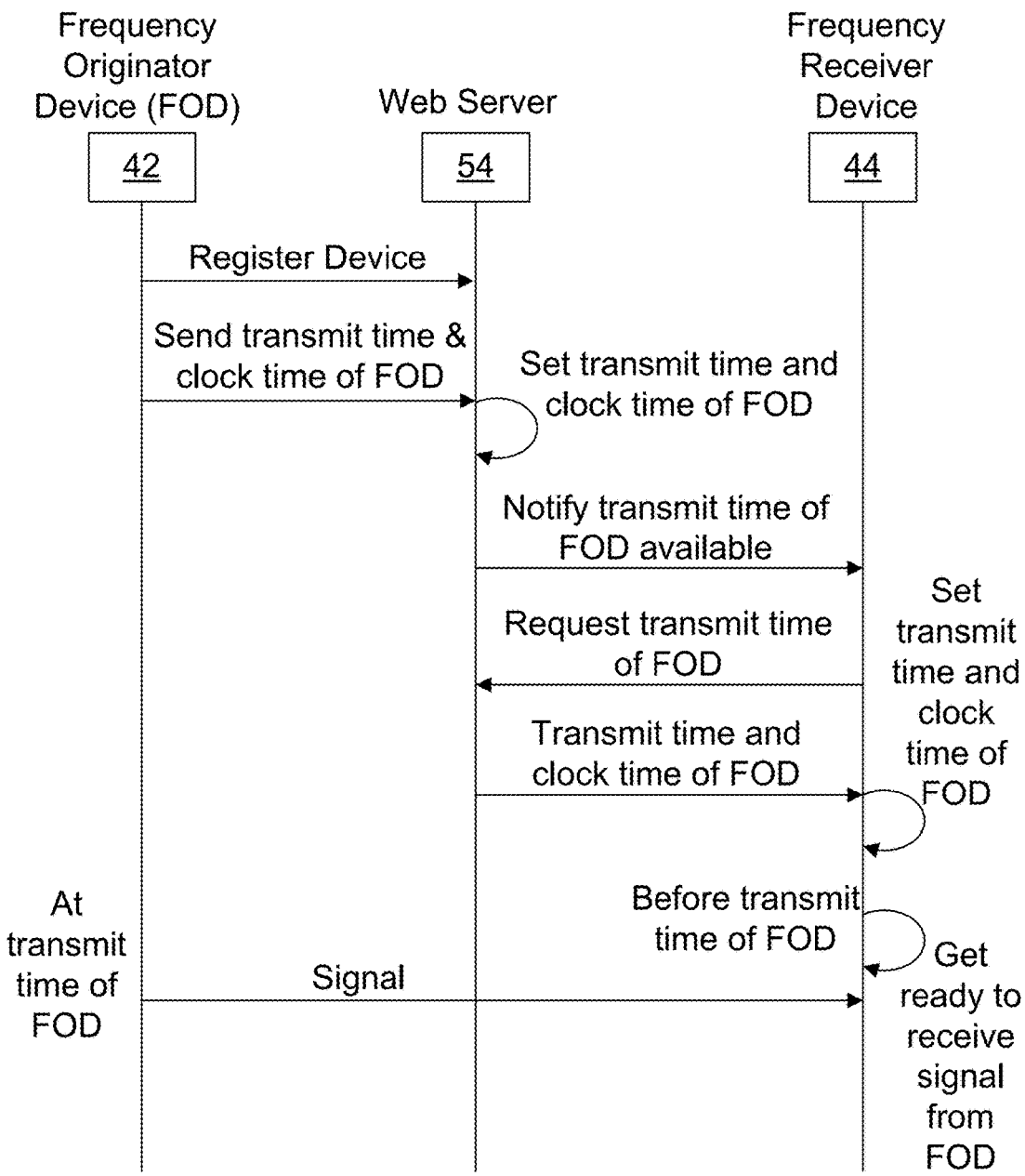
FIG. 19 is a sequence diagram depicting a means by which two devices are clock time synchronized via a web server.

FIG. 19 is a sequence diagram depicting a means by which two devices are clock time synchronized via a web server. In this example, one of the devices is a frequency originator device and the other, a frequency receiver device. Each of the frequency originator device and frequency receiver device can be a mobile device or a fixed device. The frequency originator device is first registered with a web server with some form of identification. A transmit time (the time at which a signal is to be broadcasted by the frequency originator device) is then sent to the web server where the transmit time is then associated with this frequency originator device. The web server is configured to notify the frequency receiver device that a frequency originator device is ready to make a signal broadcast. As the frequency receiver device is interested in receiving the broadcast, it responds by sending a request to the web server for the transmit time and clock time of the frequency originator device. Such information is sent to the frequency receiver device. Upon receiving such information, the transmit time and clock time are saved and used to set appropriate functions to anticipate the arrival of a signal from the frequency originator device. It shall be noted that the clock time is a time stamp in which latencies due to transmissions of this information from the frequency originator device to the frequency receiver device has been considered. The frequency receiver device is then put in a ready and standby state prior to the transmit time of the signal such that upon the arrival of the signal, the frequency receiver device is ready to receive and process the signal.

Figure 20:
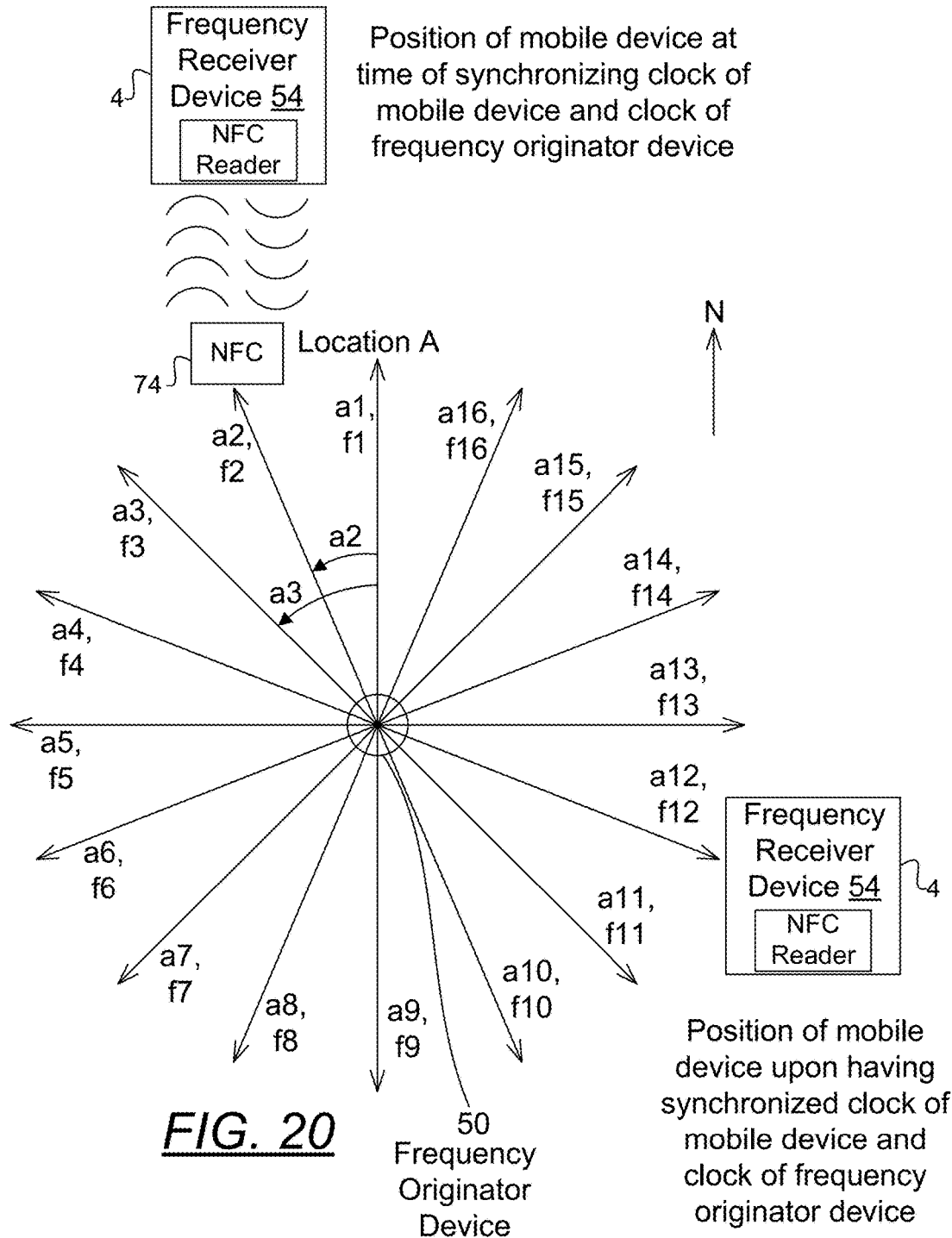
FIG. 20 is a diagram depicting one embodiment of a present localization system including the use of an information storage device.
Figure 21:
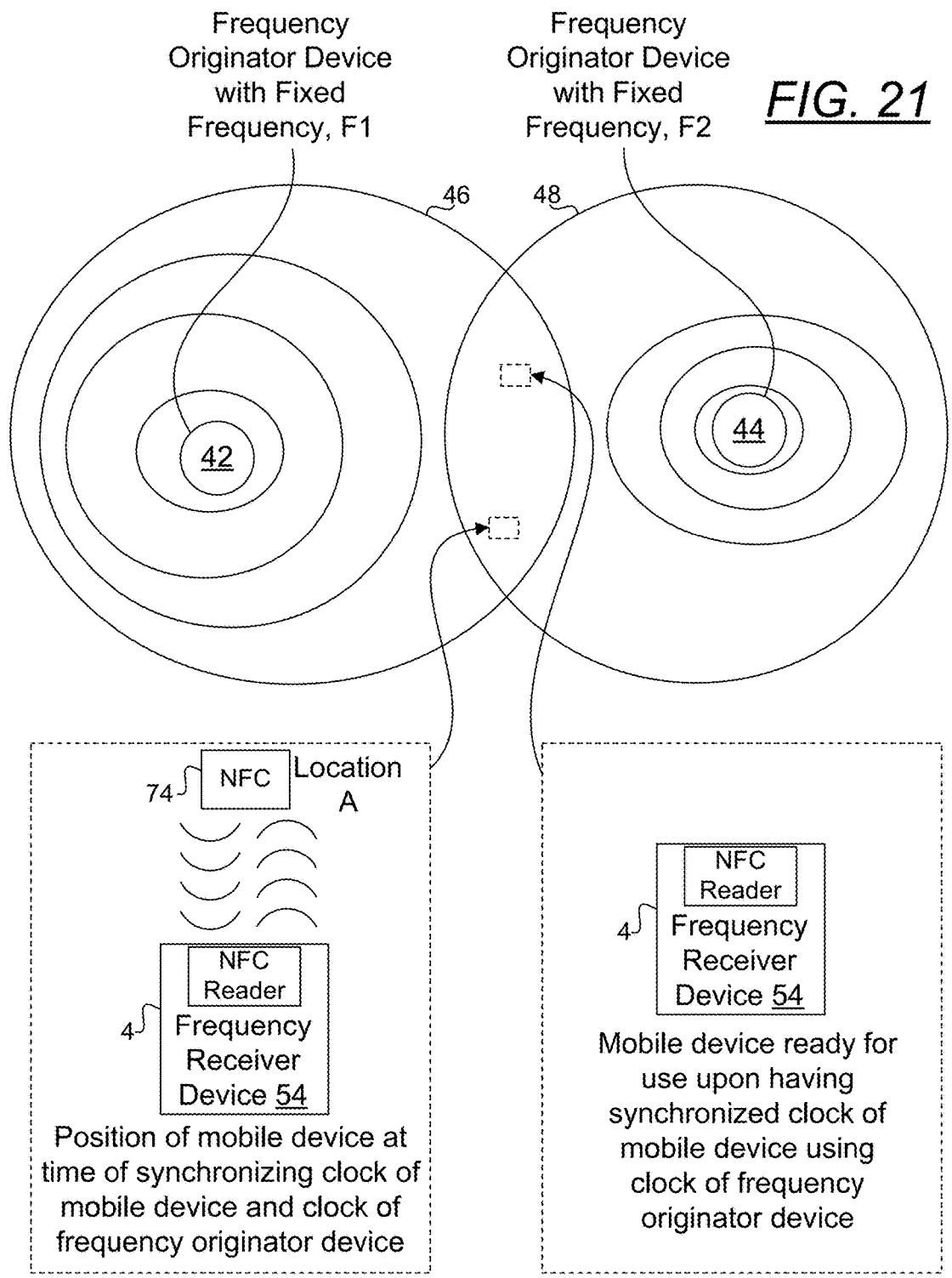
FIG. 21 is a diagram depicting another embodiment of a present localization system including the use of an information storage device.

FIG. 20 is a diagram depicting one embodiment of a present localization system including the use of an information storage device 74. FIG. 21 is a diagram depicting another embodiment of a present localization system including the use of an information storage device. In one example, a frequency originator device or a frequency receiver device is a stand-alone device which includes its own controller and is not coupled with a mobile device. In another example, a frequency originator device or a frequency receiver device is coupled to a mobile device, e.g., cell phone, electronic pad, etc. In the latter example, computations and other processing activities required by the frequency originator and receiver devices may be made in the mobile device, removing the need to require separate controllers in the frequency originator and receiver devices. In the configurations shown in FIGS. 14 and 15, clock synchronizing of the frequency receiver device by the frequency originator device may be performed by communicating the clock time of one device (frequency originator device or frequency receiver device) to another, via, e.g., the internet. In cases where no such communication is available or desired to either one or both of the devices, clock synchronizing is made possible by the following process. The distance between a frequency originator device and a frequency receiver device is first predetermined and stored in an information storage device 74 along with the carrier frequency of the frequency originator device. A time correction 70 is then calculated from a message received by the frequency receiver device from the frequency originator device based on the transmit time of the message that is embedded in the message and the TOF that is calculated based on the distance between the frequency originator device and the frequency receiver device and the speed of transmission of the message. In one embodiment, the information storage device 74 is a short-range Radio Frequency Identification (RFID) tag. In one embodiment, the RFID tag is a Near Field Communication (NFC) tag. An NFC tag is preferred as it is unpowered, does not require contact with its reader to function and yet it requires that its reader to be placed in close proximity to function, thereby indicating that when disposed in close proximity to a reader, the reader's location is essentially the NFC's location. Disclosed herein is a localization system where the location of a frequency receiver device is first obtained, similar to the manner in which a location is obtained for each of frequency receiver devices A and B shown in FIG. 14 and the frequency receiver devices shown in FIG. 15. Referring to FIG. 20, as the carrier frequency of messages is programmed to vary according to the angle at which the messages are broadcasted, the location of the frequency receiver device relative to the frequency originator device can be determined based on the carrier frequency at which messages are received by the frequency receiver device and the distance of between the frequency originator device and the frequency receiver device. As NFC is a very short range contactless data transfer technology, the placement of an NFC tag at a location previously associated with a frequency receiver device as identified using a frequency originator device-frequency receiver device pair as shown in FIGS. 14 and 15, provides a close approximation of the NFC tag's location. In this example, a NFC tag is disposed at location A. The use of an NFC tag removes the reliance on other means for accessing information, i.e., via the internet regarding the carrier frequency or a range of carrier frequencies of messages transmitted from the frequency originator device and distance between the frequency originator device and the frequency receiver device or the NFC tag which is now placed in place of a frequency receiver device which was used to identify such distance. Such information is instead stored in the NFC tag. In use, a passerby or user armed with an NFC reader, can bring the reader in the vicinity of NFC tag to within range, e.g., about 4 cm, to initiate a handshake and obtain the information stored in the NFC tag.

Figure 22:
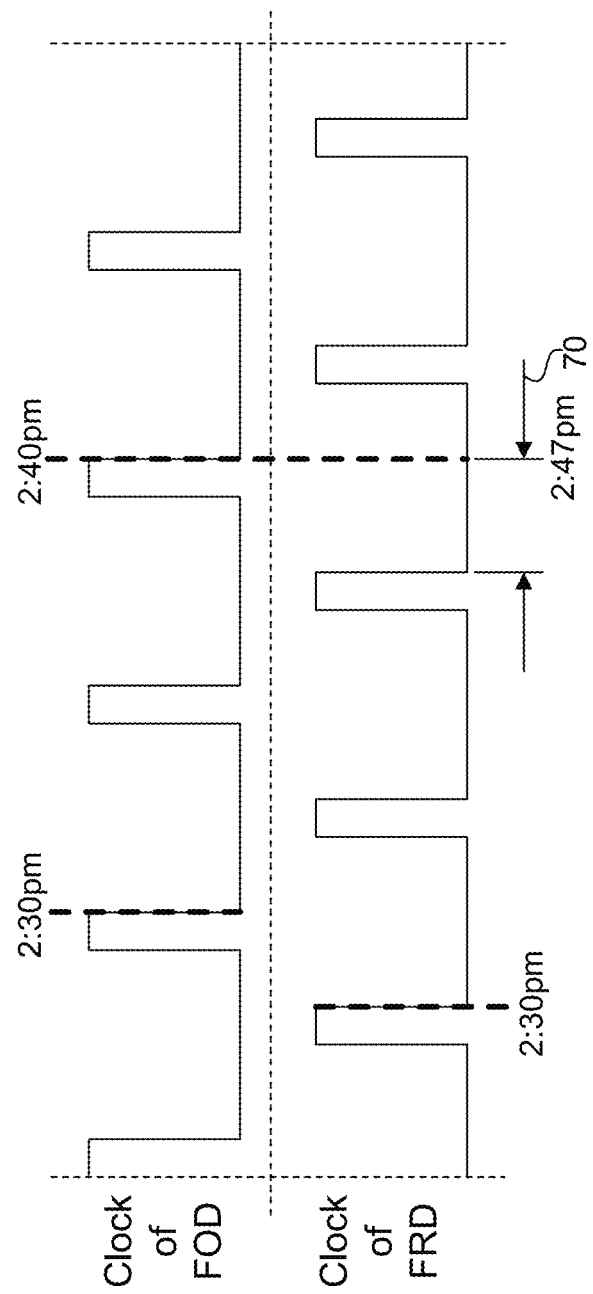
FIG. 22 is a diagram depicting an example of a correction that is required to be made to synchronize the clock of a frequency originator device and a frequency receiver device.

Armed with the distance d and a known speed s for the traversal of messages sent from the frequency originator device to the frequency receiver device, a TOF can be calculated e.g., via communications tool or application already built into or that is otherwise available on a mobile device, e.g., cell phone, to which the NFC reader is functionally connected, according to the equation $s=d/TOF$ or $TOF=d/s$ where d=distance between the frequency originator device and the NFC tag and s represents the speed of a message traversing the distance between the frequency originator device and the NFC tag or if sound waves are used, s is a known value or s=speed of sound. Upon obtaining the TOF, a time correction for the frequency receiver device can be calculated as follows. When a message is determined to be of a carrier frequency the same as that specified by the NFC tag, the frequency receiver device is set to receive it and proceeds to process it. The message which is believed to be originating from the frequency originator device contains the clock time $t1$ at which the message started to get transmitted from the frequency originator device. Assume $T2$ is the clock time at which the frequency receiver device received the message. The frequency originator device's clock time at the time the frequency receiver device received the message is $t1+TOF$. Therefore, the frequency originator device's clock time and the frequency receiver device's clock time differs by a time correction of $(T2-(t1+TOF))$. FIG. 22 is a diagram depicting an example of a time correction that is required to be made to synchronize the clock of a frequency originator device and a frequency receiver device. For instance, as shown in FIG. 22, at any moment, the clock time of the frequency originator device differs from the clock time of the frequency receiver device by a correction amount, e.g., 7 minutes (or 420 seconds) in this case. Once a time correction has been obtained, the frequency receiver device can be used to indicate its location. A user carrying the frequency receiver device can then be moved around an area within the transmission range of the frequency originator device and be tracked using the frequency originator device. For instance, if a message is starting to be transmitted from the frequency originator device at the frequency originator device's clock time of $t3$ and received at the frequency receiver device's clock time of $T4$, the TOF of the message can be obtained by subtracting $t3$ from $T4$ with the time correction applied or $TOF=T4-t3+$time correction. If more than one frequency originator device is used, additional NFC tags may be used, each storing a set of information pertinent to one frequency originator device. Alternatively, all necessary clock time synchronizing information for all frequency originator devices in one area is contained within only one NFC tag. For users' convenience, multiple NFC tags may be disposed at various locations provided each has been stored pertinent information for the particular locations the NFC tags have been placed. When NFC tags are used to store information pertaining to the carrier frequency and distance to the frequency originator device, no access of such information is necessary via the internet. In another embodiment, each NFC contains a Universal Resource Identifier (URI) where the carrier frequency and distance to its corresponding frequency originator device are accessed via the URI. In a cell phone-equipped frequency receiver device, the access to an information storage may also be identified by a URI and accessed via a cellular network.

Figure 23:
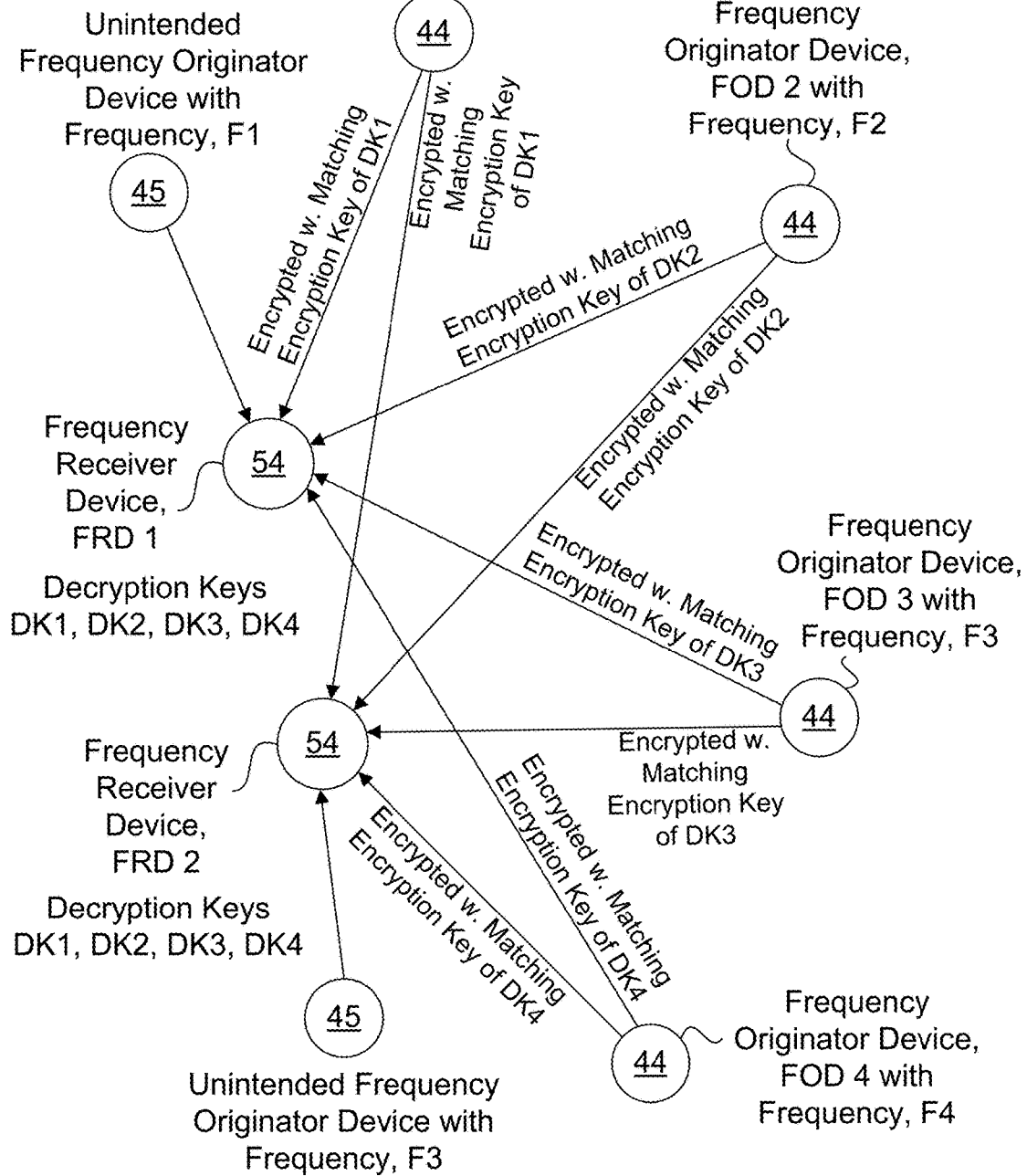
FIG. 23 is a diagram depicting the use of encryption in one embodiment of a present localization system.

FIG. 23 is a diagram depicting the use of encryption in one embodiment of a present localization system. Although encryption is shown for only the configuration of FIG. 23, it is applicable to any configurations involving the broadcast of a message from a frequency originator device where the message is then received in a frequency receiver device. In this example, a system having four frequency originator devices 44, each broadcasting messages at a unique carrier frequency, e.g., F1 for frequency originator device (FOD) 1, F2 for FOD 2, F3 for FOD 3 and F4 for FOD 4, are shown to broadcast messages subsequently received by two frequency receiver devices 54, i.e., frequency receiver device (FRD) 1 and FRD 2. Two unintended frequency originator devices are shown. Unintended frequency originator devices can be any devices broadcasting messages either as a result of a naturally occurring action or a deliberate action meant to interrupt or sabotage the use such a system to determine locations of frequency receiver devices. Unintended FODs 45 may be present within the localization system shown in FIG. 23 where such FODs may broadcast messages of carrier frequencies expected by FRDs. In a non-encrypted system, the use of a common carrier frequency can cause one or more frequency receiver devices 54 to pick up messages broadcasted by the unintended FODs 45 if these FODs are placed within the transmission range of the frequency originator devices. In one embodiment, prior to transmitting a message, it is first encrypted with an encryption key in the frequency originator device 44. A decryption key DK1, DK2, DK3, DK4 is made available to the frequency receiver devices 54 via communication means, e.g., the internet from a server, retrieving such information from an information storage device or such information may simply be preprogrammed in the frequency receiver device or made available to an information storage device, e.g., an NFC tag. Upon receipt of a message, it is decrypted using the decryption key DK1, DK2, DK3, DK4. Messages from the unintended frequency originator devices 45 may be received as their carrier frequencies may match those of the expected frequencies. However, no instructions will be available for decrypting the messages. Therefore, the messages will be ignored. It shall therefore be apparent that the present mechanism can be used to ignore irrelevant data.

Figure 24:
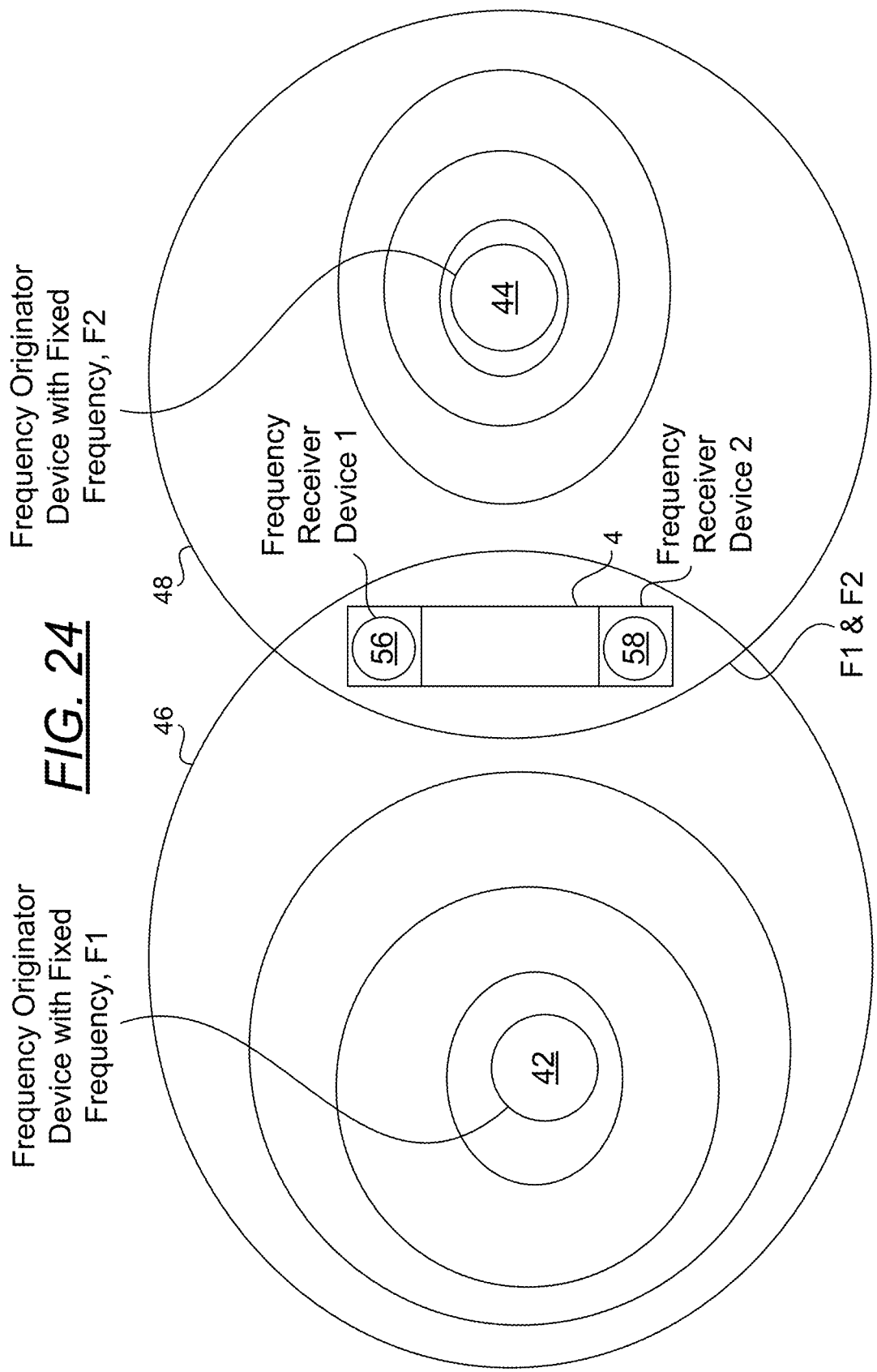
FIG. 24 is a diagram depicting another embodiment of a present localization system including the use of more than one frequency receiver device on a single mobile device.
Figure 25:
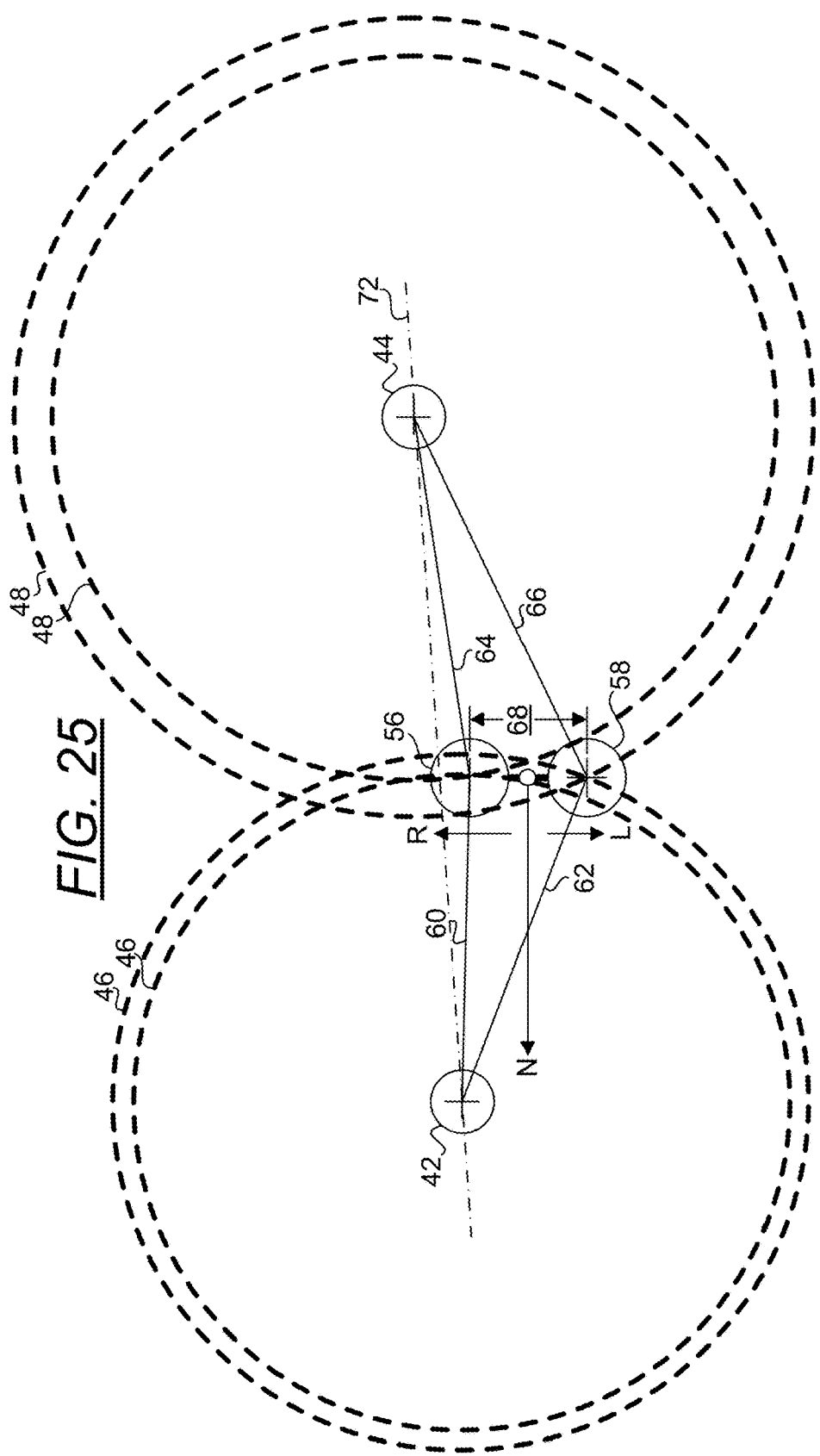
FIG. 25 is a diagram showing the embodiment of FIG. 24 depicted with distances between frequency originator and receiver devices shown where such distances can be used to uniquely identify the location of the mobile device upon which the frequency receiver devices are attached.
Figure 26:
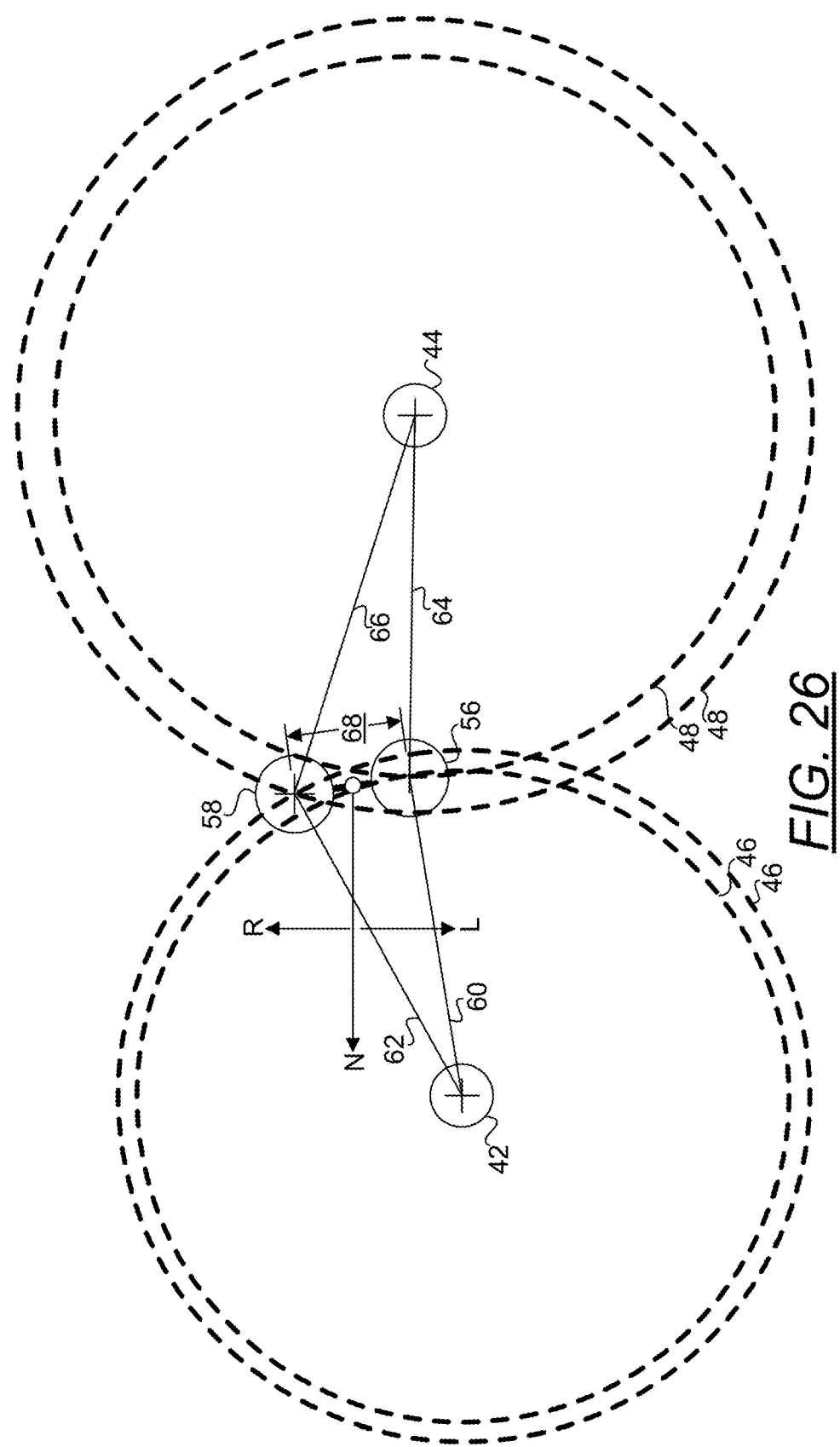
FIG. 26 is a diagram possible location of the mobile device of FIG. 25 where such possible location is eliminated by having the heading information shown in FIG. 25.

FIG. 24 is a diagram depicting another embodiment of a present localization system including the use of more than one frequency receiver device on a single mobile device 4. FIG. 25 is a diagram showing the embodiment of FIG. 24 depicted with distances between frequency originator 42, 44 and receiver 56, 58 devices shown where such distances can be used to uniquely identify the location of the mobile device 4 upon which the frequency receiver devices 56, 58 are functionally coupled. FIG. 26 is a diagram of a possible location of the mobile device of FIG. 25 where such possible location is eliminated by having the heading information shown in FIG. 25. In this embodiment, in identifying the location of the mobile device 4, it is equipped with more than one frequency receiver devices 56, 58. Only two frequency originator devices 42, 44 of known locations are required. The mobile device 4 to which each frequency receiver device 56, 58 is attached further includes a heading indicating device, e.g., magnetometer, gyrocompass etc., to further provide heading information. In one embodiment, the magnetometer is further functionally coupled with a gyroscope to remove a requirement that mobile device 4 be placed in a particular orientation so as to function properly, making it orientation-agnostic. No additional information is required, e.g., as shown in FIG. 18, to perfect the localization of the singly disposed frequency receiver devices. In one embodiment, the heading indicating device is disposed in a manner that it is physically located between the two frequency receiver devices 56, 58 as shown in FIG. 25. A pattern can be established that, in order for the distances 60, 62, 64, 66 to be disposed in the configuration shown in FIG. 25, the mobile device 4 must be disposed in a unique orientation, i.e., in the orientation shown in FIG. 25. A unique solution to the location of mobile device 4 is possible as it can be determined on which side a TOF has been collected. For instance, the TOF corresponding to distance 60 or the frequency receiver device 56 is disposed on the right side of north heading and the TOF corresponding to distance 62 or the frequency receiver device 58 is disposed on the left side of north heading. Without the heading information, it is possible that the location of the frequency receiver devices 56, 58 can be located in positions shown in FIG. 26. It is also possible that the positions of the frequency receiver devices 56, 58 can be two points in a plane traced when the two points are revolved around axis 72. With the heading information however, there can only be one solution which meets the requirements of the distances 60, 62, 64, 66. It therefore would not have been possible to have the TOFs disposed in a configuration as shown in FIG. 26, making the solution shown in FIG. 25 unique. With two frequency receiver devices 56, 58 disposed at detected distances 60, 62 from the first originator device 42 and detected distances 64, 66 from the second originator device 44, the availability of a heading indicating device enables possible locations of the mobile device 4 to be eliminated. In one embodiment, a frequency originator device 42, 44 is a music box, such as the one disclosed in U.S. Pat. No. 5,449,856 to Nakamori.

Figure 27:
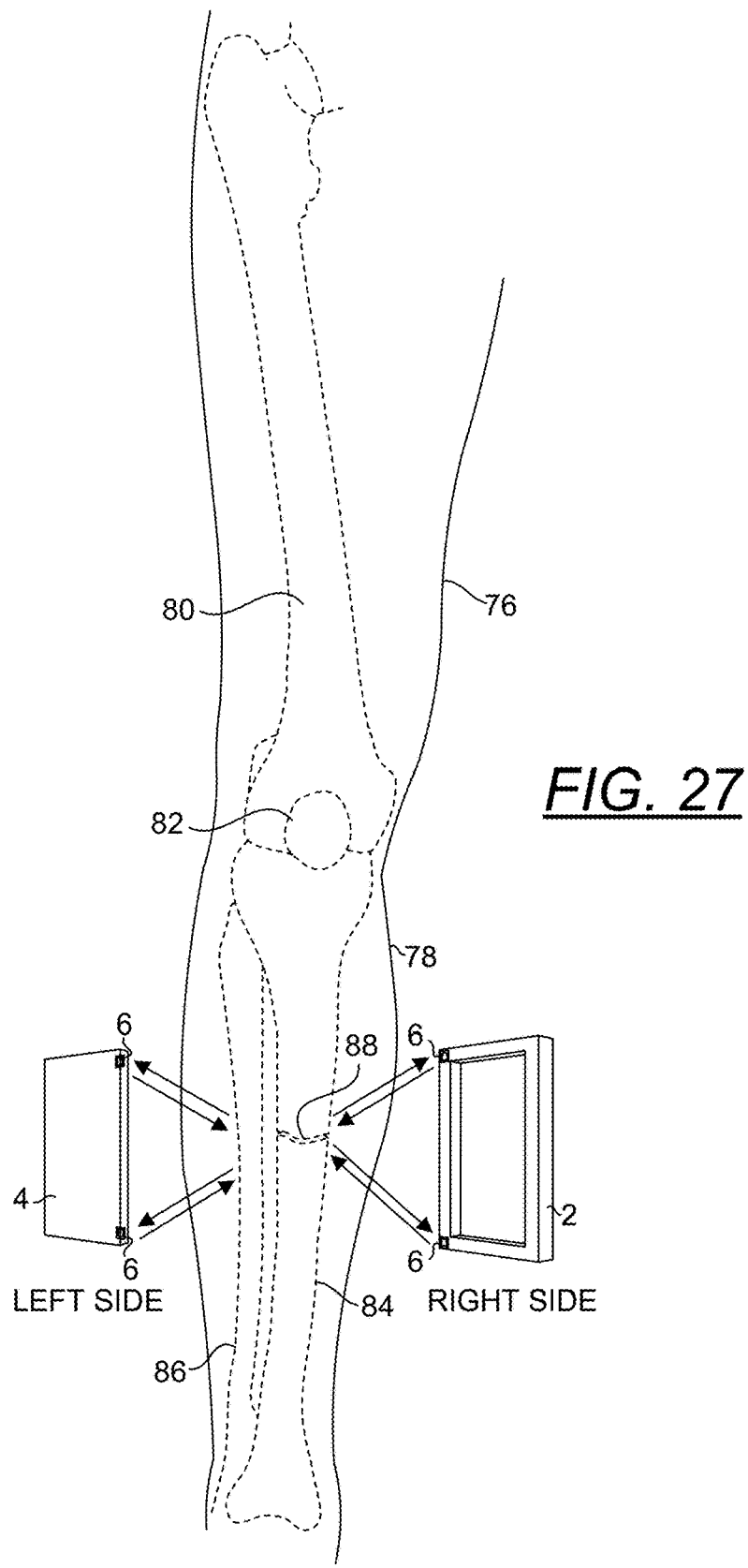
FIG. 27 is a diagram depicting another usage example of the devices shown in FIGS. 1 and 2.

FIG. 27 is a partially transparent partial view of a patient's thigh 76, leg 78, femur 80, patella 82, tibia 84 and fibula 86, depicting another usage example of the devices shown in FIGS. 1 and 2. Again, while used as a protector, the mobile device 4 is typically seated in the cradle of the case 2. However, when equipped with an ultrasound or ultrasonic transducer 6 (e.g., ultrasonic transceiver), each of the mobile device 4 and case 2 can be used individually to produce tomographs. Sounds waves are represented by arrows with transmitted waves as arrows emanating from either one of the devices 2, 4 and echoes as arrows culminating at one of the devices. The genesis of echoes received at a first transceiver may be transmitted waves of a first transceiver itself or the transmitted waves of a second transceiver of the same device. When combined, tomographs generated from both a mobile device 4 and a case 2 either functionally coupled or not functionally coupled to the mobile device 4 can be used to confirm the validity of tomographs obtained from one another. When functionally coupled, tomographs obtained from the mobile device 4 and case 2 may be automatically time-synched. Time synching of the two devices 2, 4 can take the form, e.g., of interleaving the transmitting-receiving cycles of each of the two devices 2, 4 and operating the transmitting-receiving cycles of each of the two devices 2, 4 simultaneously. Time-synching can also be used between the transceivers of each device 2, 4. As shown herein, an ultrasound imaging of a suspected broken leg is desired. The tibia is shown to have a break 88. There are three major parts of the leg 78, i.e., the fibula 86, tibia 84 and the soft tissue surrounding the fibula 86 and tibia 84. The mobile device 4 is removed from its case 2 and the mobile device 4 and case 2 are disposed on opposing sides of the subject to be scanned with the transducers 6 of a mobile device 4 or case 2 pointed towards the subject to be scanned. An additional apparatus, e.g., a rod with clamps may additionally be used for holding the mobile device 4 and the case 2 in place while performing scanning to ease the burden of holding the devices 2, 4 at roughly consistent distances. Reference is made to article "Basics of Ultrasound Imaging" by Vincent Chan et al. of the "Atlas of Ultrasound-Guided Procedures in Interventional Pain Management," ISBN: 978-1-4419-1679-2 (hereinafter US Imaging) for basic principles of ultrasound imaging and problems associated with ultrasound, especially when an ultrasound device is used from a single direction or a limited range of directions. US Imaging details refraction artifacts (seen on FIG. 2.5 of US Imaging) and posterior acoustic enhancement artifacts (seen on FIG. 2.7 of US Imaging). An ultrasonic transducer 6 can work both as a speaker (for generating sound waves) and a microphone (for receiving sound waves). As shown in FIG. 27, it is also possible to equip a mobile device or a case with more than one transducer. In one aspect, each transducer can produce a set of tomographs, i.e., the sound waves transmitted from the transducer are received by the speaker of the same transducer and the received waves can be processed to produce a first set of tomographs. In a second aspect, when a first transducer 6 of either a mobile device 4 or case 2 is functionally coupled with a second transducer 6 of the same mobile device 4 or case 2, a second set of tomographs can be produced. As there are two transducers 6 on a mobile device 4, a total of four sets of tomographs can be obtained (i.e., two first sets of tomographs and two second sets of tomographs). Generated tomographs may be individually viewed in real time or stored in a memory device of either the mobile device 4 or the case 2 for viewing at a later time. Various image overlay or pattern matching techniques, e.g., edge detection techniques, may also be applied to overlay detected features (e.g., specific bones, cavities) to overcome the artifacts disclosed in US Imaging.

Figure 28:
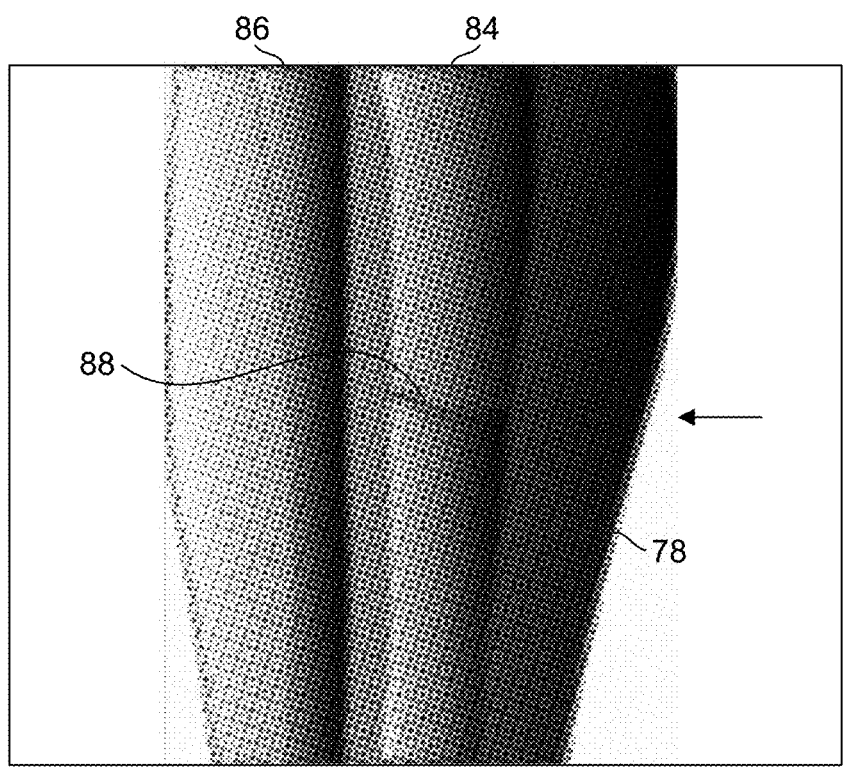
FIG. 28 is a diagram depicting an ultrasound imaging example obtained with a mobile device case disposed on one side (RIGHT SIDE) of a human body portion as shown in FIG. 27.
Figure 29:
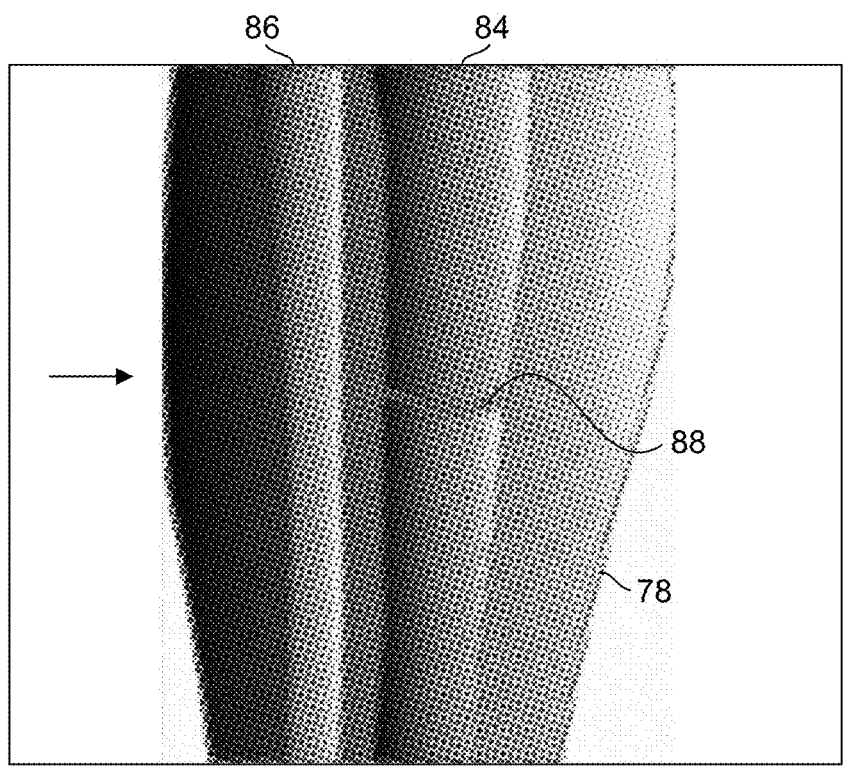
FIG. 29 is a diagram depicting an ultrasound imaging example obtained with a mobile device case disposed on an opposing side (LEFT SIDE) of the human body portion as shown in FIG. 27.

FIG. 28 is a diagram depicting an ultrasound imaging example or tomograph obtained with a mobile device case disposed on one side of the leg as shown in FIG. 27. FIG. 29 is a diagram depicting an ultrasound imaging example or tomograph obtained with a mobile device that is disposed on the opposing side of the leg as shown in FIG. 27. The arrow in each of FIGS. 28 and 29 represents the direction from which imaging data is collected. It shall be noted that the surfaces facing a transducer are more densely plotted or darker, indicating that the reflections of ultrasound from the bones and soft tissue are more readily generated on surfaces facing the transducer and therefore more available to be received at the devices 2, 4. When used together, the tomographs generated from both the mobile device and case complement one another as one tomograph is obtained from a first direction and shows a first view and the other that is obtained from a second direction that generates a second view that is at least partially obscured from the first direction.

Figure 30:
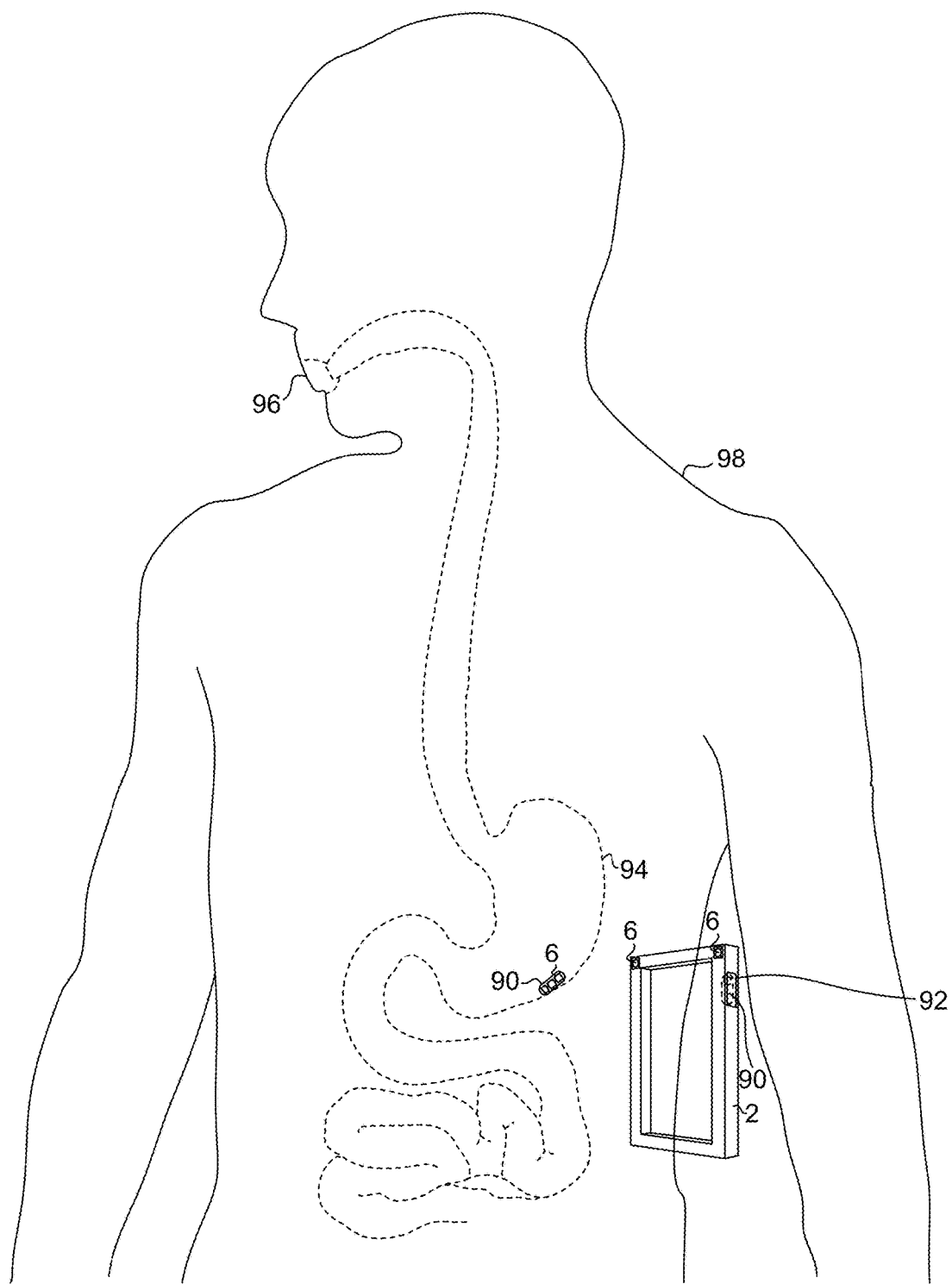
FIG. 30 is a diagram depicting yet another usage example of the devices shown in FIGS. 1 and 2.
Figure 31:
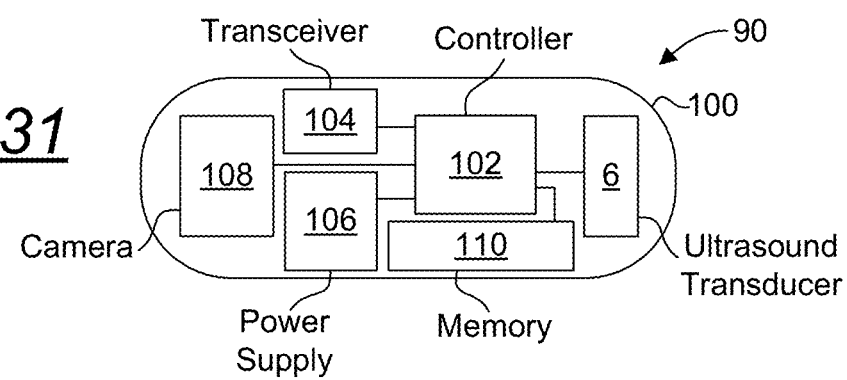
FIG. 31 is a diagram depicting one embodiment of a miniature pill and its internal components.

FIG. 30 is a diagram depicting yet another usage example of the devices shown in FIGS. 1 and 2. In this example, a sensor-equipped miniature medical grade pill 90 is functionally coupled to case 2 and/or mobile device 4 to perform one or more functions. The pill 90 can be equipped with one or more devices, e.g., an imaging device, e.g., a camera and an ultrasound transducer, etc. When not in use, the pill 90 is disposed in a receptacle 92 on the case 2 for storage. In use, the pill 90 is swallowed via the mouth 96 of the patient 98 and as it moves through the gastrointestinal tract of the patient 98, images may be collected via the imaging device and transmitted to the mobile device for real time inspection or storage. In one embodiment, the case 2 may serve as a signal booster station where weak or limited communication from the pill 90 may be relayed to the mobile device for display and/or storage. As such, the pill can be made as small in size as possible as it is not required to communicate over great distances and the transmitter and receiver can be fabricated at micro or nano scale. The case 2 can be held at close proximity to the swallowed pill 90 outside of (the torso of) the patient 98 while the mobile device 4 can be disposed at a greater distance from the pill 90 for viewing, for instance, while held in by a medical professional. FIG. 31 is a diagram depicting one embodiment of a miniature pill and its internal components. The pill 90 includes a protective shell 100, within which a plurality of components are disposed. There is provided a controller 102 capable of functional connection with a mobile device case and/or a mobile device via a transceiver 104. The pill 90 can have an ultrasound transducer 6 and a camera 108, each functionally connected to the controller 102. Images obtained via camera 108 may be transmitted in real time to the mobile device or they can be stored in a memory 110 functionally connected to the controller 102 for transmission at a later time. Similarly, data received at the ultrasound transducer or transceiver 6 may also be transmitted in real time to the mobile device or stored in the memory 110 for transmission at a later time. As the pill 90 is capable of being swallowed, its ultrasound transceiver 6 offers views, e.g., via tomographs (generated subsequently from data collected via the ultrasound transceiver 6) not available from an ultrasound transceiver disposed outside of a human body. Again, pattern matching of tomographs obtained from a pill 90 disposed in a hard-to-reach location and an ultrasound transceiver 6 disposed at a location and orientation complementing that of the pill 90, may be performed to further correlate views of the tomographs to provide one or more resulting enhanced images that show more clearly details of the subject. The pill 90 may be used in any hard-to-reach locations, e.g., in a human body, animal body, plumbing system, hazardous area, etc.

Figure 32:
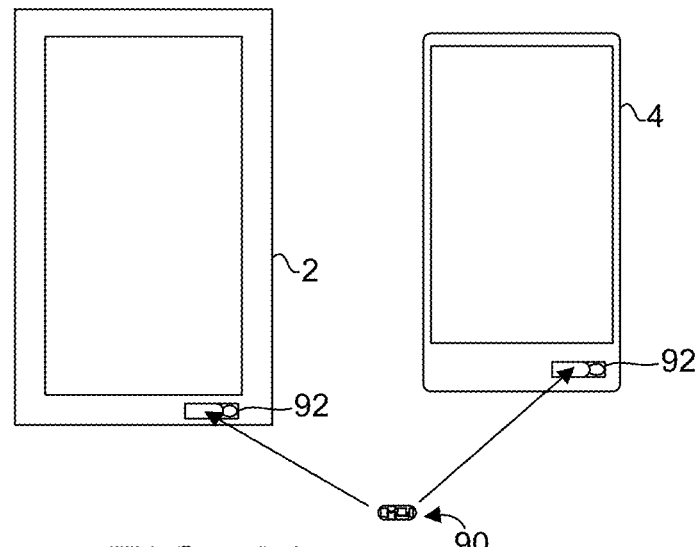
FIG. 32 is a diagram depicting one embodiment of a transducer capable of operation outside of a mobile device or a mobile device case to which the transducer can be functionally and physically coupled.

FIG. 32 is a diagram depicting one embodiment of a transducer capable of operation outside of a mobile device or a mobile device case to which the transducer can be functionally and physically coupled. A mobile device 4 or a mobile device case 2 may alternatively include a receptacle 92 for receiving or storing a separate device, e.g., a sensor-equipped pill 90 while pill 90 is not in use. The sensor-equipped pill 90 may alternatively be equipped with a wireless charging device such that its power supply 106 requires no direct contact with a charging device available on the mobile device 4, mobile device case 2 or another charging station. Once hermatically sealed, e.g., during fabrication, the internals of a sensor-equipped device, e.g., pill 90, can continue to be used without risk of exposure to elements. FIGS. 30-32 demonstrate a sensor (e.g., any one of the sensors encapsulated in pill 90) capable of functional connection with either a mobile device 4 or a mobile device case 2.

While the methods, systems and devices have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

Throughout this application, various publications are referenced. The disclosures of these publications in their entireties are hereby incorporated by reference into this application in order to more fully describe the state of the art to which the methods and systems pertain.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following inventive concepts.

What is claimed herein is:

1. A mobile device case for functional connection and physical attachment to a mobile device, said mobile device case comprises:
   (a) an application adapted to run in the mobile device; and
   (b) a cradle configured for removable attachment with the mobile device, said cradle comprising a controller capable of wireless functional connection with said application,
   whereby said cradle is configured to protect the mobile device while attached to the mobile device and said cradle is configured to functionally pair with said application to create at least a portion of a mesh network and said wireless functional connection comprises communicating a message from said controller of said cradle of said mobile device case to said application; calculating a time of flight of said message; and comparing said time of flight to an expected time of flight to yield a discrepancy, whereby if said discrepancy is greater than a predetermined value, an action is initiated by at least one of said application and said mobile device case.

2. The mobile device case of claim 1, further comprising at least one sensor functionally connected to said controller of said cradle.

3. The mobile device case of claim 2, wherein said at least one sensor is an ultrasound transducer.

4. The mobile device case of claim 2, wherein said at least one sensor is selected from the group consisting of an accelerometer, a directional antennae and an imaging device.

5. The mobile device case of claim 1, further comprising at least one socket for receiving at least one sensor, wherein said at least one socket is functionally connected to said controller of said cradle.

6. The mobile device case of claim 1, further comprising a second functional connection of said controller of said cradle with said application that is wired.

7. The mobile device case of claim 1, further comprising a data transmitter and a data receiver, wherein said data transmitter is configured to initiate a communication with a data receiver of the mobile device and said data receiver is configured to receive a communication with a data transmitter of the mobile device.

8. The mobile device case of claim 1, wherein said wireless functional connection is made according to a communication protocol selected from the group consisting of Bluetooth and wireless local area network (Wi-Fi).

9. The mobile device case of claim 1, wherein said wireless functional connection further comprises:
   (a) communicating a message from said application to said cradle of said mobile device case;
   (b) calculating a time of flight of said message; and
   (c) comparing said time of flight to an expected time of flight to yield a discrepancy,
   whereby if said discrepancy is greater than a predetermined value, an action is initiated by at least one of said application and said mobile device case.

10. The mobile device case of claim 1, further comprising a sensor-equipped miniature medical grade pill configured for traversal through the gastrointestinal tract of a human body, wherein said sensor-equipped miniature medical grade pill comprises a controller adapted for functional connection with one of said controller of said cradle and the mobile device.

11. A mobile device case for functional connection and physical attachment to a mobile device, said mobile device case comprises:
   (a) an application adapted to run in the mobile device;
   (b) a cradle configured for removable attachment with the mobile device, said cradle comprising a controller capable of functional connection with said application; and
   (c) a sensor-equipped miniature medical grade pill configured for traversal through the gastrointestinal tract of a human body, wherein said sensor-equipped miniature medical grade pill comprises a controller adapted for functional connection with one of said controller of said cradle and the mobile device,
   whereby said cradle is configured to protect the mobile device while attached to the mobile device and said cradle is configured to functionally pair with said application to create at least a portion of a mesh network.

12. The mobile device case of claim 11, further comprising at least one ultrasound transducer adapted to be functionally connected to the mobile device.

13. The mobile device case of claim 11, further comprising at least one sensor functionally connected to said controller of said cradle.

14. The mobile device case of claim 13, said at least one sensor is capable of wireless functional connection with one of said controller of said cradle and the mobile device.

15. The mobile device case of claim 13, wherein said at least one sensor is selected from the group consisting of an accelerometer, a directional antennae, an ultrasound transducer and an imaging device.

16. The mobile device case of claim 11, wherein said functional connection of said controller of said cradle with said application comprises:
   (a) communicating a message from said controller of said cradle of said mobile device case to said application;
   (b) calculating a time of flight of said message; and
   (c) comparing said time of flight to an expected time of flight to yield a discrepancy,
   whereby if said discrepancy is greater than a predetermined value, an action is initiated by at least one of said application and said mobile device case.

17. The mobile device case of claim 11, wherein said functional connection of said controller of said cradle with said application comprises:
   (a) communicating a message from said application to said cradle of said mobile device case;
   (b) calculating a time of flight of said message; and
   (c) comparing said time of flight to an expected time of flight to yield a discrepancy,
   whereby if said discrepancy is greater than a predetermined value, an action is initiated by at least one of said application and said mobile device case.

18. The mobile device case of claim 11, further comprising at least one ultrasound transducer functionally connected to said controller of said cradle.

19. The mobile device case of claim 11, further comprising at least one socket for receiving at least one sensor, wherein said at least one socket is functionally connected to said controller of said cradle.

20. The mobile device case of claim 11, wherein said functional connection of said controller of said cradle with said application is wired.

21. The mobile device case of claim 11, wherein said functional connection of said controller of said cradle with said application is wireless.

22. The mobile device case of claim 21, further comprising a data transmitter and a data receiver, wherein said data transmitter is configured to initiate a communication with a data receiver of the mobile device and said data receiver is configured to receive a communication with a data transmitter of the mobile device.

23. The mobile device case of claim 21, wherein said functional connection of said controller of said cradle with said application is made according to a communication protocol selected from the group consisting of Bluetooth and wireless local area network (Wi-Fi).

24. A mobile device case for functional connection and physical attachment to a mobile device, said mobile device case comprises:
  (a) an application adapted to run in the mobile device; and
  (b) a cradle configured for removable attachment with the mobile device, said cradle comprising a controller capable of wireless functional connection with said application,
  whereby said cradle is configured to protect the mobile device while attached to the mobile device and said cradle is configured to functionally pair with said application to create at least a portion of a mesh network and said wireless functional connection comprises communicating a message from said application to said cradle of said mobile device case; calculating a time of flight of said message; and comparing said time of flight to an expected time of flight to yield a discrepancy, whereby if said discrepancy is greater than a predetermined value, an action is initiated by at least one of said application and said mobile device case.

25. The mobile device case of claim 24, further comprising at least one sensor functionally connected to said controller of said cradle.

26. The mobile device case of claim 25, wherein said at least one sensor is an ultrasound transducer.

27. The mobile device case of claim 25, wherein said at least one sensor is selected from the group consisting of an accelerometer, a directional antennae and an imaging device.

28. The mobile device case of claim 24, further comprising at least one socket for receiving at least one sensor, wherein said at least one socket is functionally connected to said controller of said cradle.

29. The mobile device case of claim 24, further comprising a data transmitter and a data receiver, wherein said data transmitter is configured to initiate a communication with a data receiver of the mobile device and said data receiver is configured to receive a communication with a data transmitter of the mobile device.

30. The mobile device case of claim 24, wherein said wireless functional connection is made according to a communication protocol selected from the group consisting of Bluetooth and wireless local area network (Wi-Fi).

31. The mobile device case of claim 24, wherein said wireless functional connection further comprises:
  (a) communicating a message from said controller of said cradle of said mobile device case to said application;
  (b) calculating a time of flight of said message; and
  (c) comparing said time of flight to an expected time of flight to yield a discrepancy,
  whereby if said discrepancy is greater than a predetermined value, an action is initiated by at least one of said application and said mobile device case.

32. The mobile device case of claim 24, further comprising a sensor-equipped miniature medical grade pill configured for traversal through the gastrointestinal tract of a human body, wherein said sensor-equipped miniature medical grade pill comprises a controller adapted for functional connection with one of said controller of said cradle and the mobile device.

* * * * *